US007662601B2

(12) United States Patent
Krokan et al.

(10) Patent No.: US 7,662,601 B2
(45) Date of Patent: Feb. 16, 2010

(54) DNA GLYCOSYLASES AND THEIR USE

(76) Inventors: Hans E. Krokan, Unigen Center for Molecular Biology, University of Trondheim, Trondheim (NO) N-7005; Geir Slupphaug, Unigen Center for Molecular Biology, University of Trondheim, Trondheim (NO) N-7005; Bodil Kavli, Unigen Center for Molecular Biology, University of Trondheim, Trondheim (NO) N-7005; John A. Tainer, The Scripps Ranch Research Institute, 10666 N. Torrey Pines Rd., La Jolla, CA (US) 92037; Clifford D. Mol, The Scripps Ranch Research Institute, 10666 N. Torrey Pines Rd., La Jolla, CA (US) 92037

( * ) Notice: Subject to any disclaimer, the term of this patent is extended or adjusted under 35 U.S.C. 154(b) by 1000 days.

(21) Appl. No.: 10/746,239

(22) Filed: Dec. 23, 2003

(65) Prior Publication Data

US 2006/0134631 A1    Jun. 22, 2006

Related U.S. Application Data

(62) Division of application No. 09/101,368, filed as application No. PCT/GB97/00057 on Jan. 9, 1997, now Pat. No. 6,713,294.

(30) Foreign Application Priority Data

Jan. 9, 1996 (GB) ................................. 9600384.3

(51) Int. Cl.
*C12N 9/10* (2006.01)
*C12N 15/00* (2006.01)
*C12P 21/04* (2006.01)
*C12P 19/34* (2006.01)
*C12Q 1/68* (2006.01)
*C12Q 1/48* (2006.01)
*C07H 21/04* (2006.01)
*C12Q 1/00* (2006.01)
*C12N 1/20* (2006.01)
*C07H 21/02* (2006.01)

(52) U.S. Cl. ................. 435/193; 435/4; 435/6; 435/15; 435/69.1; 435/71.1; 435/252.3; 435/320.1; 435/440; 435/91.2; 536/23.2; 536/23.1

(58) Field of Classification Search ............ None
See application file for complete search history.

(56) References Cited

U.S. PATENT DOCUMENTS

| 5,278,784 A | 1/1994 | Ishihara et al. ................. 365/96 |
| 5,418,738 A | 5/1995 | Abadeer et al. ............. 365/100 |
| 5,646,438 A | 7/1997 | Frerichs ...................... 257/530 |
| 5,748,025 A | 5/1998 | Ng et al. ...................... 327/333 |
| 5,886,392 A | 3/1999 | Schuegraf ................... 257/530 |
| 5,898,611 A | 4/1999 | Yamada ...................... 365/154 |
| 5,949,712 A | 9/1999 | Rao et al. .............. 365/185.07 |
| 5,963,462 A | 10/1999 | Engh et al. ..................... 365/45 |
| 6,041,008 A | 3/2000 | Marr ........................ 365/225.7 |
| 6,044,012 A | 3/2000 | Rao et al. ................... 365/182 |
| 6,087,890 A | 7/2000 | Kim ............................ 327/526 |
| 6,130,834 A | 10/2000 | Mullarkey et al. ............ 365/96 |
| 6,181,627 B1 | 1/2001 | Casper et al. ............ 365/225.7 |
| 6,188,265 B1 | 2/2001 | Liu et al. ...................... 327/390 |
| 6,266,269 B1 | 7/2001 | Karp et al. ................... 365/150 |
| 6,400,605 B1 | 6/2002 | Adkins ................... 365/185.18 |
| 6,445,622 B1 | 9/2002 | Hirano .................. 365/189.11 |
| 6,525,955 B1 | 2/2003 | Smith et al. .................... 365/96 |
| 6,639,866 B2 | 10/2003 | Slamowitz et al. ...... 365/230.05 |

FOREIGN PATENT DOCUMENTS

| EP | 624643 | 11/1994 |
| EP | 0756379 A | 1/1997 |
| WO | WO 93/18175 | 9/1993 |
| WO | WO/02/063689 A1 | 8/2002 |

OTHER PUBLICATIONS

Mol et al. Crystal structure and mutational analysis of human uracil-DNA glycosylase: structural basis for specificity and catalysis. Cell. Mar. 24, 1995;80(6):869-78.*
Branden et al. Introduction to Protein Structure, Garland Publishing Inc., New York, p. 247, 1991.*
Bhagwat et al., *Journal of Bacteriology* 169(4):1537-1546 (1987).
Bjelland et al., *The Journal of Biological Chemistry* 269(48):30489-30495 (1994).
Boiteux et al., *The Journal of Biological Chemistry* 265(7):3916-3922 (1990).
Cannon et al. *Biochemical and Biophysical Research Communications* 151(3):1173-1179 (1998).
Da Roze et al., *Biochemistry* 16(22):4934-4939 (1977).
Duncan et al., *Journal of Bacteriology* 134(3):1039-1045 (1978).
Duncan, *Journal of Bacteriology* 164(2):689-695 (1985).
Eftedal et al., *Nucleic Acid Research* 21(9):2095-2101 (1993).
Haug et al., FEBS Lett. 353:180-184 (1994).
Haug et al., *Genomics* 36:408-416 (1996).
International Search Report mailed on Aug. 20, 1997 for PCT patent application No. PCT/GB97/00057 filed on Jan. 9, 1997, 2 pages.
Kavli et al., *The EMBO Journal* 15(13):3442-3447 (1996).
Lowell et al., *Infection and Immunity* 1706-1713 (1996).
Lowell et al., *Science* 240:800-802. (1988).
Lowell, *Presentation of Peptide and Protein Vaccines* 141-160. (1990).
Mallett et al., *Infection and Immunity* 2382-2386 (1995).
McDonald et al., Locus, Accession No. Z65719 (Oct. 1995).
Mejean et al., *Molecular Microbiology* 11(2):323-330 (1994).
Mejean et al., *Nucleic Acid Research* 18(22):6693 (1990).
Mejean et al., *Nucleic Acid Research* 19(20):5525-5531 (1991).

(Continued)

*Primary Examiner*—Yong D Pak
(74) *Attorney, Agent, or Firm*—Morrison & Foerster LLP

(57) ABSTRACT

Novel cytosine-, thymine- and uracil-DNA glycosylases, subcellular localization peptides, nucleic acid molecules containing the same, methods of identifying such enzymes and their use in various methods including mutagenesis, cell killing and DNA sequencing and modification, are desired.

12 Claims, 7 Drawing Sheets

OTHER PUBLICATIONS

Figure 1:
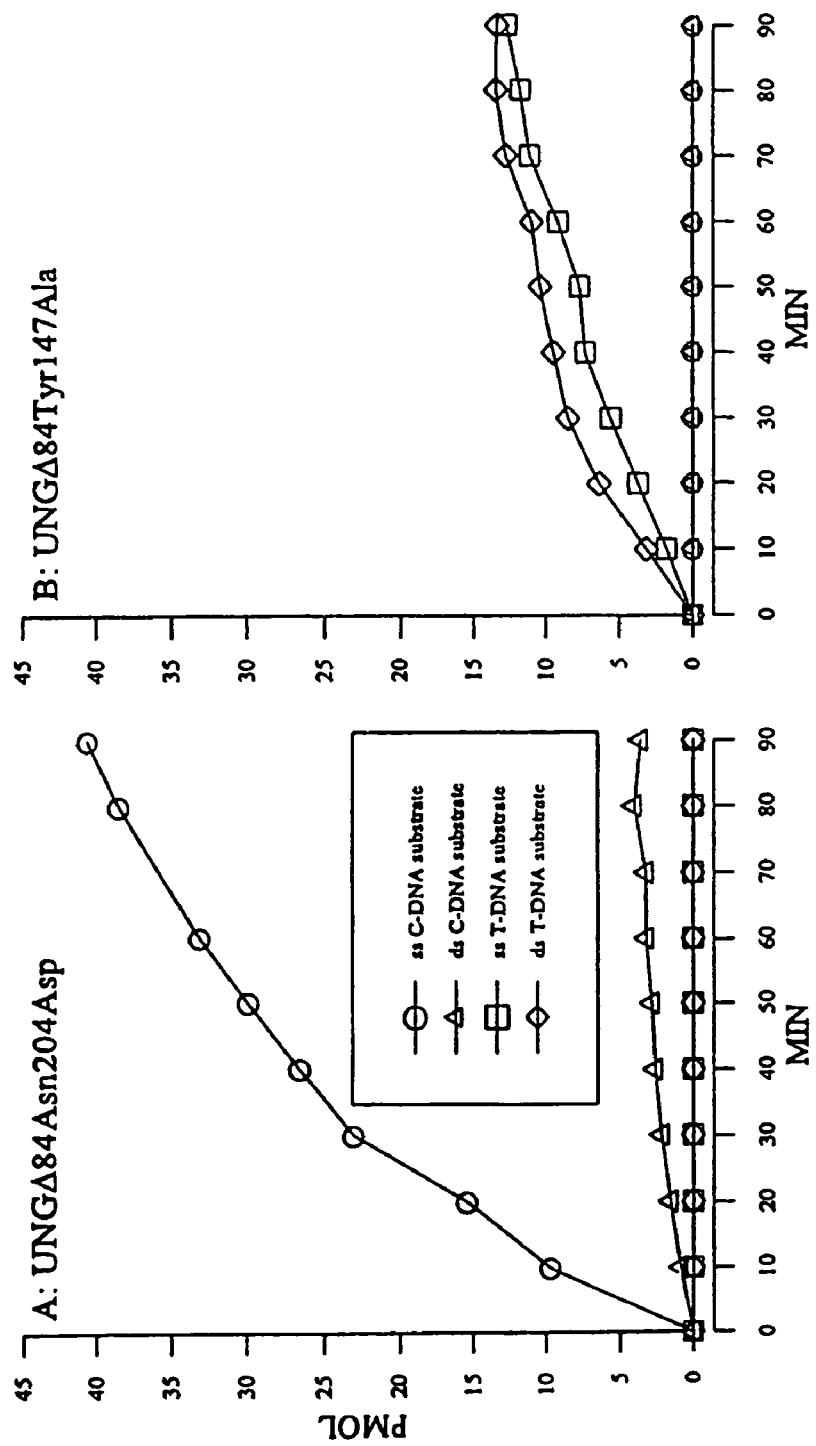

Mol et al., *Cell* 80:869-878 (1995).
Mol et al., *Cell* 82:701-708 (1995).
Nagelhus et al., *Experimental Cell Research* 220:292-297 (1995).
Nedderman et al., *J. Biol. Chem.* 268:21218-21224 (1993).
Nedderman et al., *J. Proc. Natl. Acad. Sci.* 91:1642-1646 (1994).
Neddermann et al., *PNAS* 91:1642-1646 (1994).
Nilsen et al., *FEBS Letters* 362:205-209 (1995).
Olivera et al., *J. Mol. Biol.* 128:265-275 (1979).
Olsen et al., *EMBO J*, 8(10):3121-3125 (1989).
Olsen et al., *Nucleic Acid Research* 19(16):4473-4478 (1991).
Patricia Foster, *Journal of Bacteriology* 172(8):4719-4720 (1990).
Roy et al., *Biochemistry* 33:15131-15140 (1994).
Sassanfar et al., *J. Mol. Biol.* 212:79-96 (1990).
Savva et al., *Nature* 373:487-493 (1995).
Simmons et al., *Journal of Bacteriology* 137(3):1243-1252 (1979).
Slupphaug et al., *Biochemistry* 34:128-138 (1995).
Slupphaug et al., *Nucl. Acids. Res.* 21(11):2579-2584 (1993).
Taylor et al., *Journal of Bacteriology* 151(1):351-357 (1982).
Wang et al., *BioTechniques* 7(9):1000-1010(1989).
Warner et al., *Journal of Bacteriology* 145(2):687-695 (1981).
Wei et al., Locus, Accession No. U19783 (Jul. 1995).
Weiss et al., Biochemistry 28:1488-92 (1989).
Wittwer et al., *Biochemistry* 28:780-784 (1989).

\* cited by examiner

Figure 5

```
301  tcaagctcactacagctcagaccctctggcctcaagcgatcctccagcctggcctccaaagcgctaggattacaggcgtggccaccgcgcctgacc
                                                                                            AP2      C-MYB
401  agtctttctcttgcagctgagccttaagagcagagagtggctgaaggcacaaagcgaatgaaagaataggccccgggaccgtt
                                      AP2                            SP1    SP1/AP2
501  gcacgccccacctcctccagggcgttgcactccagccctcccgcacatgcgcactgggcttccacgcccccgccccagcaaagccccccgctc
                        CCAAT                              Start of exon 1A
                                                         ┌→
                                                PEA3
601  ggagcatgcgcgggcgcttggcgcccaattgctgaccgcCAGCCTAGCCTCGCCAGCCCACAGCGCCACAGCCTCGCCAGGGCTAGCCCTGCCCTC
        ↑ Start codon 1A
             PU.1/PEA3
701  AGCTCCAGGATGATCGGCCTCTACTCCTTTTCTCCCCAGCCCCCCGAGCCCCCAGAAGCGACACGCGCCGACACGCGCCCCGAGCCCGTCCAGGGA
              PU.1
801  CCGGCGTGGCTGGGGTGCCTGAGGAAAGCGGAGATCGGCGgtgaggcgcggcttgggccgggcgcttgggccgggcgcttgggccgggcgcttgg
                                          AP1                   C-MYC  REPRESSOR(RPA)
901  cctgacgcgagggcgtgcaggatcgcgccctctgactcggtaaacccggctccgctttccaaatagcctcacgtgttcaaaatagccgctgtccccc
                                                                                         YY1       CCA
     AP2    YY1              CCAAT
1001 atgggccgccatgctaaaggggccaatggaacgctctcggggccatggccaatccgcgccaggccctcctgcctcggtgcgctgtcca
     AT AGAGGG AGAGGG   SP1    AGAGGG          E2F  C-MYC                       SP1        SP1
1101 atcagaggggagggggcggcaggagaccagaggaggtttttgccgcgaaagaccacgtggggacgcggtggggcttcttgccgggggcggggcacctc
                                                YY1                              Start of exon 1B   CCAAT
                                                                             ┌→
1201 tgtgcagggttccagtcaccgcgacgctcctcggaagccataggcgc CTCCCAGCCCGTCTCCCCGCTCCAGTTAGAACCTAATTCCCAATTCCC
                                                       ↑ Start codon 1B
1301 GACCGGGCCCAGCCCTGGCTCTTACTGTCCGCTTTTGCTGGGACCTGTTCCACACAAATGGGGCGTCTTCTGCCTTGGGCCGTTGGGCCGGAAGCT
                                                                                  ↘ Alternative splice acceptor site
1401 GCGGACCCGCTGGGAAGGGCCGCCCTCTGCAGCTCTTGAGCCCGTGACCACTTGCAGGCCATCCCAGCCAAGAAGGCCCCGGCTGGGCAGGAGGAG
1501 CCTGGGACCCGCTCCTCGCCGCTGAGTGCCGAGCAGTTGGACCGGATCCAGAGGAACAAGGCCGGCGGCCCTGCTCAGACTCGCGGCCCCAACGTGC
1601 CCGTGGGCTTGGAGAGCTGGAAGAGCACCTCAGCGGGGAGTTCGGGAAACCGTATTTTATCAAGgtaaatatgaaatgcaccttccataaggta
```

|          |                                                      |         |
|----------|------------------------------------------------------|---------|
| hUNG1    | *MGVFCLGPWGLGRKLRTPGKGPLQLLSRLC----GDHLQA*           | 36      |
| mUNG1    | *MGV-------LGRRSLR--LARRAGLRSLTPNPDSDSRQA*           | 31      |
| hUNG2    | *MIGQKTLYSFFSPSPARKRHAPSPEPAVQGTGVAGVPEESGDAAA*      | 45      |
| mUNG2    | *MIGQKTLYSFFSPTPTGKRTTRSPEP-VPGSGVAA--EIGGDAVA*      | 42      |
|          |                                                      |         |
| hUNG2/1  | IPAKKAPAGQEEPGTPPSSPLSAEQLDRIQRNKAAALLRLAARNV        | 90/81   |
| mUNG2/1  | SPAKKARVEQNEQG----SPLSAEQLVRIQRNKAAALLRLAARNV        | 83/72   |
|          |                                                      |         |
| hUNG2/1  | PVGFGESWKKHLSGEFGKPYFIKLMGFVAEERKHYTVYPPPHQVF        | 135/126 |
| mUNG2/1  | PAGFGESWKQQLCGEFGKPYFVKLMGFVAEERNHHKVYPPPEQVF        | 128/117 |
|          |                                                      |         |
| hUNG2/1  | TWTQMCDIKDVKVVILGQDPYHGPNQAHGLCFSVQRPVPPPPSLE        | 180/171 |
| mUNG2/1  | TWTQMCDIRDVKVVILGQDPYHGPNQAHGLCFSVQRPVPPPPSLE        | 173/162 |
|          |                                                      |         |
| hUNG2/1  | NIYKELSTDIEDFVHPGHGDLSGWAKQGVLLLNAVLTVRAHQANS        | 225/216 |
| mUNG2/1  | NIFKELSTDIDGFVHPGHGDLSGWARQGVLLLNAVLTVRAHQANS        | 218/207 |
|          |                                                      |         |
| hUNG2/1  | HKERGWEQFTDAVVSWLNQNSNGLVFLLWGSYAQKKGSAIDRKRH        | 270/261 |
| mUNG2/1  | HKERGWEQFTDAVVSWLNQNLSGLVFLLWGSYAQKKGSVIDRKRH        | 263/252 |
|          |                                                      |         |
| hUNG2/1  | HVLQTAHPSPLSVYRGFFGCRHFSKTNELLQKSGKKPIDWKEL          | 313/304 |
| mUNG2/1  | HVLQTAHPSPLSVYRGFLGCRHFSKANELLQKSGKKPINWKEL          | 306/295 |

Figure 6

SEQUENCE LISTING

<160> NUMBER OF SEQ ID NOS: 10

<210> SEQ ID NO 1
<211> LENGTH: 2053
<212> TYPE: DNA
<213> ORGANISM: Homo sapiens
<220> FEATURE:
<221> NAME/KEY: CDS
<222> LOCATION: (71)..(1009)

<400> SEQUENCE: 1
cacagccaca gccagggcta gcctcgccgg ttcccgggtg gcgcgcgttc gctgcctcct      60
cagctccagg atg atc ggc cag aag acg ctc tac tcc ttt ttc tcc ccc     109
            Met Ile Gly Gln Lys Thr Leu Tyr Ser Phe Phe Ser Pro
            1               5                   10

```
agc ccc gcc agg aag cga cac gcc ccc agc ccc gag ccg gcc gtc cag     157
Ser Pro Ala Arg Lys Arg His Ala Pro Ser Pro Glu Pro Ala Val Gln
    15                  20                  25 ggg acc ggc gtg gct ggg gtc cct gag gaa agc gga gat gcg gcg gcc     205
Gly Thr Gly Val Ala Gly Val Pro Glu Glu Ser Gly Asp Ala Ala Ala
 30                  35                  40                  45 atc cca gcc aag aag gcc ccg gct ggg cag gag gag cct ggg acg ccg     253
Ile Pro Ala Lys Lys Ala Pro Ala Gly Gln Glu Glu Pro Gly Thr Pro
                 50                  55                  60 ccc tcc tcg ccg ctg agt gcc gag cag ttg gac cgg atc cag agg aac     301
Pro Ser Ser Pro Leu Ser Ala Glu Gln Leu Asp Arg Ile Gln Arg Asn
             65                  70                  75 aag gcc gcg gcc ctg ctc aga ctc gcg gcc cgc aac gtg ccc gtg ggc     349
Lys Ala Ala Ala Leu Leu Arg Leu Ala Ala Arg Asn Val Pro Val Gly
         80                  85                  90 ttt gga gag agc tgg aag aag cac ctc agc ggg gag ttc ggg aaa ccg     397
Phe Gly Glu Ser Trp Lys Lys His Leu Ser Gly Glu Phe Gly Lys Pro
     95                 100                 105 tat ttt atc aag cta atg gga ttt gtt gca gaa gaa aga aag cat tac     445
Tyr Phe Ile Lys Leu Met Gly Phe Val Ala Glu Glu Arg Lys His Tyr
110                 115                 120                 125 act gtt tat cca ccc cca cac caa gtc ttc acc tgg acc cag atg tgt     493
Thr Val Tyr Pro Pro Pro His Gln Val Phe Thr Trp Thr Gln Met Cys
                130                 135                 140 gac ata aaa gat gtg aag gtt gtc atc ctg gga cag gat cca tat cat     541
Asp Ile Lys Asp Val Lys Val Val Ile Leu Gly Gln Asp Pro Tyr His
            145                 150                 155 gga cct aat caa gct cac ggg ctc tgc ttt agt gtt caa agg cct gtt     589
Gly Pro Asn Gln Ala His Gly Leu Cys Phe Ser Val Gln Arg Pro Val
        160                 165                 170 ccg cct ccg ccc agt ttg gag aac att tat aaa gag ttg tct aca gac     637
Pro Pro Pro Pro Ser Leu Glu Asn Ile Tyr Lys Glu Leu Ser Thr Asp
    175                 180                 185 ata gag gat ttt gtt cat cct ggc cat gga gat tta tct ggg tgg gcc     685
Ile Glu Asp Phe Val His Pro Gly His Gly Asp Leu Ser Gly Trp Ala
190                 195                 200                 205 aag caa ggt gtt ctc ctt ctc aac gct gtc ctc acg gtt cgt gcc cat     733
Lys Gln Gly Val Leu Leu Leu Asn Ala Val Leu Thr Val Arg Ala His
                210                 215                 220 caa gcc aac tct cat aag gag cga ggc tgg gag cag ttc act gat gca     781
Gln Ala Asn Ser His Lys Glu Arg Gly Trp Glu Gln Phe Thr Asp Ala
            225                 230                 235 gtt gtg tcc tgg cta aat cag aac tcg aat ggc ctt gtt ttc ttg ctc     829
Val Val Ser Trp Leu Asn Gln Asn Ser Asn Gly Leu Val Phe Leu Leu
        240                 245                 250 tgg ggc tct tat gct cag aag aag ggc agt gcc att gat agg aag cgg     877
Trp Gly Ser Tyr Ala Gln Lys Lys Gly Ser Ala Ile Asp Arg Lys Arg
    255                 260                 265 cac cat gta cta cag acg gct cat ccc tcc cct ttg tca gtg tat aga     925
His His Val Leu Gln Thr Ala His Pro Ser Pro Leu Ser Val Tyr Arg
270                 275                 280                 285 ggg ttc ttt gga tgt aga cac ttt tca aag acc aat gag ctg ctg cag     973
Gly Phe Phe Gly Cys Arg His Phe Ser Lys Thr Asn Glu Leu Leu Gln
                290                 295                 300 aag tct ggc aag aag ccc att gac tgg aag gag ctg tgatcatcag         1019
Lys Ser Gly Lys Lys Pro Ile Asp Trp Lys Glu Leu
            305                 310 ctgaggggtg gcctttgaga agctgctgtt aacgtatttg ccagttacga agttccactg 1079 aaaatttttcc tattaattct taagtactct gcataagggg gaaaagcttc cagaaagcag 1139
```

-continued

```
ccatgaacca ggctgtccag gaatggcagc tgtatccaac cacaaacaac aaaggctacc    1199
ctttgaccaa atgtctttct ctgcaacatg gcttcggcct aaaatatgca agacagat     1259 gaggtcaaat actcagttgg ctctctttat ctcccttgcc tttatggtga acaggggag    1319 atgtgcacct ttcaggcaca gccctagttt ggcgcctgct gctccttggt tttgcctggt   1379
tagactttca gtgacagatg ttggggtgtt tttgcttaga aaggtcccct tgtctcagcc   1439
ttgcagggca ggcatgccag tctctgccag ttccactgcc cccttgatct ttgaaggagt   1499
cctcaggccc ctcgcagcat aaggatgttt tgcaactttc cagaatctgg cccagaaatt   1559
agggctcaat ttcctgattg tagtagaggt taagattgct gtgagcttta tcagataaga   1619
gaccgagaga agtaagctgg gtcttgttat tccttgggtg ttggtggaat aagcagtgga   1679
atttgaacaa ggaagaggag aaaagggaat tttgtcttta tggggtgggg tgattttctc   1739
ctagggttat gtccagttgg ggttttttaag gcagcacaga ctgccaagta ctgttttttt   1799
taaccgactg aaatcacttt gggatatttt ttcctgcaac actggaaagt tttagttttt   1859
taagaagtac tcatgcagat atatatatat atatttttcc cagtcctttt tttaagagac   1919
ggtctttatt gggtctgcac ctccatcctt gatcttgtta gcaatgctgt ttttgctgtt   1979
agtcgggtta gagttggctc tacgcgaggt ttgttaataa agtttgtta aaagttcaaa    2039 aaaaaaaaaa aaaa                                                     2053
```

<210> SEQ ID NO 2
<211> LENGTH: 313
<212> TYPE: PRT
<213> ORGANISM: Homo sapiens

<400> SEQUENCE: 2

```
Met Ile Gly Gln Lys Thr Leu Tyr Ser Phe Phe Ser Pro Ser Pro Ala
  1               5                  10                  15

Arg Lys Arg His Ala Pro Ser Pro Glu Pro Ala Val Gln Gly Thr Gly
             20                  25                  30

Val Ala Gly Val Pro Glu Glu Ser Gly Asp Ala Ala Ile Pro Ala
         35                  40                  45

Lys Lys Ala Pro Ala Gly Gln Glu Glu Pro Gly Thr Pro Ser Ser
     50                  55                  60

Pro Leu Ser Ala Glu Gln Leu Asp Arg Ile Gln Arg Asn Lys Ala Ala
 65                  70                  75                  80

Ala Leu Leu Arg Leu Ala Ala Arg Asn Val Pro Val Gly Phe Gly Glu
                 85                  90                  95

Ser Trp Lys Lys His Leu Ser Gly Glu Phe Gly Lys Pro Tyr Phe Ile
            100                 105                 110

Lys Leu Met Gly Phe Val Ala Glu Glu Arg Lys His Tyr Thr Val Tyr
        115                 120                 125

Pro Pro Pro His Gln Val Phe Thr Trp Thr Gln Met Cys Asp Ile Lys
    130                 135                 140

Asp Val Lys Val Val Ile Leu Gly Gln Asp Pro Tyr His Gly Pro Asn
145                 150                 155                 160

Gln Ala His Gly Leu Cys Phe Ser Val Gln Arg Pro Val Pro Pro
                165                 170                 175

Pro Ser Leu Glu Asn Ile Tyr Lys Glu Leu Ser Thr Asp Ile Glu Asp
            180                 185                 190

Phe Val His Pro Gly His Gly Asp Leu Ser Gly Trp Ala Lys Gln Gly
        195                 200                 205
```

```
Val Leu Leu Leu Asn Ala Val Leu Thr Val Arg Ala His Gln Ala Asn
        210                 215                 220

Ser His Lys Glu Arg Gly Trp Glu Gln Phe Thr Asp Ala Val Val Ser
225                 230                 235                 240

Trp Leu Asn Gln Asn Ser Asn Gly Leu Val Phe Leu Leu Trp Gly Ser
                245                 250                 255

Tyr Ala Gln Lys Lys Gly Ser Ala Ile Asp Arg Lys Arg His His Val
                260                 265                 270

Leu Gln Thr Ala His Pro Ser Pro Leu Ser Val Tyr Arg Gly Phe Phe
            275                 280                 285

Gly Cys Arg His Phe Ser Lys Thr Asn Glu Leu Leu Gln Lys Ser Gly
        290                 295                 300

Lys Lys Pro Ile Asp Trp Lys Glu Leu
305                 310

<210> SEQ ID NO 3
<211> LENGTH: 132
<212> TYPE: DNA
<213> ORGANISM: Homo sapiens
<220> FEATURE:
<221> NAME/KEY: CDS
<222> LOCATION: (1)..(132)

<400> SEQUENCE: 3 atg atc ggc cag aag acg ctc tac tcc ttt ttc tcc ccc agc ccc gcc    48
Met Ile Gly Gln Lys Thr Leu Tyr Ser Phe Phe Ser Pro Ser Pro Ala
 1               5                  10                  15 agg aag cga cac gcc ccc agc ccc gag ccg gcc gtc cag ggg acc ggc    96
Arg Lys Arg His Ala Pro Ser Pro Glu Pro Ala Val Gln Gly Thr Gly
             20                  25                  30 gtg gct ggg gtg cct gag gaa agc gga gat gcg gcg                   132
Val Ala Gly Val Pro Glu Glu Ser Gly Asp Ala Ala
         35                  40

<210> SEQ ID NO 4
<211> LENGTH: 44
<212> TYPE: PRT
<213> ORGANISM: Homo sapiens

<400> SEQUENCE: 4

Met Ile Gly Gln Lys Thr Leu Tyr Ser Phe Phe Ser Pro Ser Pro Ala
 1               5                  10                  15

Arg Lys Arg His Ala Pro Ser Pro Glu Pro Ala Val Gln Gly Thr Gly
             20                  25                  30

Val Ala Gly Val Pro Glu Glu Ser Gly Asp Ala Ala
         35                  40

<210> SEQ ID NO 5
<211> LENGTH: 105
<212> TYPE: DNA
<213> ORGANISM: Homo sapiens
<220> FEATURE:
<221> NAME/KEY: CDS
<222> LOCATION: (1)..(105)

<400> SEQUENCE: 5 atg ggc gtc ttc tgc ctt ggg ccg tgg ggg ttg gcc gga agc tgc cgg    48
Met Gly Val Phe Cys Leu Gly Pro Trp Gly Leu Gly Arg Lys Leu Arg
 1               5                  10                  15 acg cct ggg aag ggg ccg ctg cag ctc ttg agc cgc ctc tgc ggg gac    96
Thr Pro Gly Lys Gly Pro Leu Gln Leu Leu Ser Arg Leu Cys Gly Asp
```

```
                    20                  25                  30
cac ttg cag                                                                    105
His Leu Gln
        35

<210> SEQ ID NO 6
<211> LENGTH: 35
<212> TYPE: PRT
<213> ORGANISM: Homo sapiens

<400> SEQUENCE: 6

Met Gly Val Phe Cys Leu Gly Pro Trp Gly Leu Gly Arg Lys Leu Arg
  1               5                  10                  15

Thr Pro Gly Lys Gly Pro Leu Gln Leu Leu Ser Arg Leu Cys Gly Asp
                 20                  25                  30

His Leu Gln
        35

<210> SEQ ID NO 7
<211> LENGTH: 1399
<212> TYPE: DNA
<213> ORGANISM: Homo sapiens

<400> SEQUENCE: 7
tcaaagctca ctacagctca gaccctctgg cctcaagcga tcctccagcc tgggcctccc      60
aaagcgctag gattacaggc gtgggccacc gcgcctgacc agtcttctct tcttgcagct    120
gagccttaag agcctgtcca agagcagag gtgggctgaa ggcacaaagc gaatgaaaga     180
ataggccccc gggcaccgtt gcacgcccca cctcctccca ggggcgttgc actccagccc    240
ctcccgcaca tgcgcactgg ccttccacc gcccccgcc ccagcaaag ccccccgctc       300 ggagcatgcg cgggccgctt ggcgccaatt gctgaccgcc acagccacag ccagggctag    360
cctcgccggt tcccgggtgg cgcgcgttcg ctgcctcctc agctccagga tgatcggcca    420
gaagacgctc tactcctttt tctcccccag ccccgccagg aagcgacacg ccccagccc     480 cgagccggcc gtccagggga ccggcgtggc tggggtgcct gaggaaagcg gagatgcggc    540
ggtgaggcgc ggcttgggcc ggggctaggg ggtgaagggg gaggaaggcg gtgggccccg    600
cctgacggag ggcgtgcagg atcgcgcctc tgactcggta aacccgggct ccgctttcca    660
aatagcctcc acgtgttcaa atagccgcc gctgtccccc atgggccgcc atgctaaagg     720
gccagccaat gggaacgcgt ctcggggccc atggcgccaa tccgcgcgcc gcaggccctc    780
ctggctcggt gcgctgtcca atcagagggg agaggggggcg ggacccagag ggaggttttt   840
tgccgcgaaa agaccacgtg gggacgcggt ggggcgggtc tggcggggc ggggcacctc     900 tgtgcagggt tcccagtcac cgcgacgctc tcgggaagc cataggggcgc ctcccagccc    960 gtctccccgc tccagtttag aacctaattc ccaattcccg accggcccca gccctgggct   1020
cttactgtcc gcttttgctg ggacctgttc cacaaatggg cgtcttctgc cttgggccgt   1080
gggggttggg ccggaagctg cggacgcctg ggaaggggcc gctgcagctc ttgagccgcc   1140
tctgcgggga ccacttgcag gccatcccag ccaagaaggc cccggctggg caggaggagc   1200
ctgggacgcc gccctcctcg ccgctgagtg ccgagcagtt ggaccggatc cagaggaaca   1260
aggccgcggc cctgctcaga ctcgcggccc gcaacgtgcc cgtgggcttt ggagagagct   1320
ggaagaagca cctcagcggg gagttcggga aaccgtattt tatcaaggta aatatggaaa   1380
tgcaccttcc ataagggta                                                 1399
```

<210> SEQ ID NO 8
<211> LENGTH: 304
<212> TYPE: PRT
<213> ORGANISM: Homo sapiens

<400> SEQUENCE: 8

Met Gly Val Phe Cys Leu Gly Pro Trp Gly Leu Gly Arg Lys Leu Arg
1               5                   10                  15

Thr Pro Gly Lys Gly Pro Leu Gln Leu Leu Ser Arg Leu Cys Gly Asp
            20                  25                  30

His Leu Gln Ala Ile Pro Ala Lys Lys Ala Pro Ala Gly Gln Glu Glu
        35                  40                  45

Pro Gly Thr Pro Pro Ser Ser Pro Leu Ser Ala Glu Gln Leu Asp Arg
    50                  55                  60

Ile Gln Arg Asn Lys Ala Ala Leu Leu Arg Leu Ala Ala Arg Asn
65                  70                  75                  80

Val Pro Val Gly Phe Gly Glu Ser Trp Lys Lys His Leu Ser Gly Glu
                85                  90                  95

Phe Gly Lys Pro Tyr Phe Ile Lys Leu Met Gly Phe Val Ala Glu Glu
            100                 105                 110

Arg Lys His Tyr Thr Val Tyr Pro Pro His Gln Val Phe Thr Trp
        115                 120                 125

Thr Gln Met Cys Asp Ile Lys Asp Val Lys Val Ile Leu Gly Gln
    130                 135                 140

Asp Pro Tyr His Gly Pro Asn Gln Ala His Gly Leu Cys Phe Ser Val
145                 150                 155                 160

Gln Arg Pro Val Pro Pro Pro Ser Leu Glu Asn Ile Tyr Lys Glu
                165                 170                 175

Leu Ser Thr Asp Ile Glu Asp Phe Val His Pro Gly His Gly Asp Leu
            180                 185                 190

Ser Gly Trp Ala Lys Gln Gly Val Leu Leu Leu Asn Ala Val Leu Thr
        195                 200                 205

Val Arg Ala His Gln Ala Asn Ser His Lys Glu Arg Gly Trp Glu Gln
    210                 215                 220

Phe Thr Asp Ala Val Val Ser Trp Leu Asn Gln Asn Ser Asn Gly Leu
225                 230                 235                 240

Val Phe Leu Leu Trp Gly Ser Tyr Ala Gln Lys Lys Gly Ser Ala Ile
                245                 250                 255

Asp Arg Lys Arg His His Val Leu Gln Thr Ala His Pro Ser Pro Leu
            260                 265                 270

Ser Val Tyr Arg Gly Phe Phe Gly Cys Arg His Phe Ser Lys Thr Asn
        275                 280                 285

Glu Leu Leu Gln Lys Ser Gly Lys Lys Pro Ile Asp Trp Lys Glu Leu
    290                 295                 300

<210> SEQ ID NO 9
<211> LENGTH: 295
<212> TYPE: PRT
<213> ORGANISM: Mus sp.

<400> SEQUENCE: 9

Met Gly Val Leu Gly Arg Arg Ser Leu Arg Leu Ala Arg Arg Ala Gly
1               5                   10                  15

Leu Arg Ser Leu Thr Pro Asn Pro Asp Ser Asp Ser Arg Gln Ala Ser
            20                  25                  30

```
Pro Ala Lys Lys Ala Arg Val Glu Gln Asn Glu Gln Gly Ser Pro Leu
        35                  40                  45

Ser Ala Glu Gln Leu Val Arg Ile Gln Arg Asn Lys Ala Ala Ala Leu
    50                  55                  60

Leu Arg Leu Ala Ala Arg Asn Val Pro Ala Gly Phe Gly Glu Ser Trp
65                  70                  75                  80

Lys Gln Gln Leu Cys Gly Glu Phe Gly Lys Pro Tyr Phe Val Lys Leu
                85                  90                  95

Met Gly Phe Val Ala Glu Glu Arg Asn His His Lys Val Tyr Pro Pro
                100                 105                 110

Pro Glu Gln Val Phe Thr Trp Thr Gln Met Cys Asp Ile Arg Asp Val
            115                 120                 125

Lys Val Val Ile Leu Gly Gln Asp Pro Tyr His Gly Pro Asn Gln Ala
    130                 135                 140

His Gly Leu Cys Phe Ser Val Gln Arg Pro Val Pro Pro Pro Pro Ser
145                 150                 155                 160

Leu Glu Asn Ile Phe Lys Glu Leu Ser Thr Asp Ile Asp Gly Phe Val
                165                 170                 175

His Pro Gly His Gly Asp Leu Ser Gly Trp Ala Arg Gln Gly Val Leu
                180                 185                 190

Leu Leu Asn Ala Val Leu Thr Val Arg Ala His Gln Ala Asn Ser His
            195                 200                 205

Lys Glu Arg Gly Trp Glu Gln Phe Thr Asp Ala Val Val Ser Trp Leu
    210                 215                 220

Asn Gln Asn Leu Ser Gly Leu Val Phe Leu Leu Trp Gly Ser Tyr Ala
225                 230                 235                 240

Gln Lys Lys Gly Ser Val Ile Asp Arg Lys Arg His His Val Leu Gln
                245                 250                 255

Thr Ala His Pro Ser Pro Leu Ser Val Tyr Arg Gly Phe Leu Gly Cys
            260                 265                 270

Arg His Phe Ser Lys Ala Asn Glu Leu Leu Gln Lys Ser Gly Lys Lys
    275                 280                 285

Pro Ile Asn Trp Lys Glu Leu
    290                 295

<210> SEQ ID NO 10
<211> LENGTH: 306
<212> TYPE: PRT
<213> ORGANISM: Mus sp.

<400> SEQUENCE: 10

Met Ile Gly Gln Lys Thr Leu Tyr Ser Phe Phe Ser Pro Thr Pro Thr
1               5                   10                  15

Gly Lys Arg Thr Thr Arg Ser Pro Glu Pro Val Pro Gly Ser Gly Val
                20                  25                  30

Ala Ala Glu Ile Gly Gly Asp Ala Val Ala Ser Pro Ala Lys Lys Ala
            35                  40                  45

Arg Val Glu Gln Asn Glu Gln Gly Ser Pro Leu Ser Ala Glu Gln Leu
    50                  55                  60

Val Arg Ile Gln Arg Asn Lys Ala Ala Ala Leu Leu Arg Leu Ala Ala
65                  70                  75                  80

Arg Asn Val Pro Ala Gly Phe Gly Glu Ser Trp Lys Gln Gln Leu Cys
                85                  90                  95

Gly Glu Phe Gly Lys Pro Tyr Phe Val Lys Leu Met Gly Phe Val Ala
                100                 105                 110
```

-continued

```
Glu Glu Arg Asn His His Lys Val Tyr Pro Pro Glu Gln Val Phe
        115             120             125

Thr Trp Thr Gln Met Cys Asp Ile Arg Asp Val Lys Val Ile Leu
    130             135             140

Gly Gln Asp Pro Tyr His Gly Pro Asn Gln Ala His Gly Leu Cys Phe
145             150             155             160

Ser Val Gln Arg Pro Val Pro Pro Pro Ser Leu Glu Asn Ile Phe
            165             170             175

Lys Glu Leu Ser Thr Asp Ile Asp Gly Phe Val His Pro Gly His Gly
            180             185             190

Asp Leu Ser Gly Trp Ala Arg Gln Gly Val Leu Leu Leu Asn Ala Val
            195             200             205

Leu Thr Val Arg Ala His Gln Ala Asn Ser His Lys Glu Arg Gly Trp
        210             215             220

Glu Gln Phe Thr Asp Ala Val Val Ser Trp Leu Asn Gln Asn Leu Ser
225             230             235             240

Gly Leu Val Phe Leu Leu Trp Gly Ser Tyr Ala Gln Lys Lys Gly Ser
                245             250             255

Val Ile Asp Arg Lys Arg His His Val Leu Gln Thr Ala His Pro Ser
            260             265             270

Pro Leu Ser Val Tyr Arg Gly Phe Leu Gly Cys Arg His Phe Ser Lys
            275             280             285

Ala Asn Glu Leu Leu Gln Lys Ser Gly Lys Lys Pro Ile Asn Trp Lys
    290             295             300

Glu Leu
305
```

DNA GLYCOSYLASES AND THEIR USE

This application is a divisional of U.S. application Ser. No. 09/101,368, filed on Mar. 3, 1999, now U.S. Pat. No. 6,713,294, which is a 371 of PCT application No. PCT/GB97/0057, filed on Jan. 9, 1997, which claims priority to United Kingdom Application Serial No. 9600384.3, filed on Jan. 9, 1996. Each of such applications are incorporated herein in their entirety.

This invention relates to new DNA-glycosylases, in particular new cytosine-, thymine- and uracil-DNA glycosylases, and their use for mutagenesis, for DNA modification and cell killing.

Damage to DNA arises continually throughout the cell cycle and must be recognised and repaired prior to the next round of replication to maintain the genomic integrity of the cell. DNA base damage can be recognised and excised by the ATP-dependent nucleoside excision repair systems or by base excision repair systems exemplified by the DNA glycosylases.

DNA glycosylases are enzymes that occur normally in cells. They release bases from DNA by cleaving the bond between deoxyribose and the base in DNA. Naturally occurring glycosylases remove damaged or incorrectly placed bases. This base excision repair pathway is the major cellular defense mechanism against spontaneous DNA damage.

DNA glycosylases which have been identified are directed to specific bases or modified bases. An example of a DNA glycosylase which recognizes an unmodified base is uracil DNA glycosylase (UDG), which specifically recognises uracil in DNA and initiates base excision repair by hydrolysing the N-C1'glycosylic bond linking the uracil base to the deoxyribose sugar. This creates an abasic site that is removed by a 5'-acting apurinic/apyrimidic (AP) endonuclease and a deoxyribophosphodiesterase, leaving a gap which is filled by DNA polymerase and closed by DNA ligase.

The activity of UDG serves to remove uracil which arises in DNA as a result of incorporation of dUMP instead of dTMP during replication or from the spontaneous deamination of cytosine. Deamination of cytosine to uracil creates a premutagenic U:G mismatch that, unless repaired, will cause a GC→AT transition mutation.

In vivo, UDGs specifically recognise and remove uracil from within DNA and cleave the glycosylic bond to initiate the uracil excision pathway. In vitro, UDG's can recognise and remove uracil from both single stranded DNA (ssDNA) and double-stranded DNA (dsDNA) substrates.

UDGs are ubiquitous enzymes and have been isolated from a number of sources. Amino acid sequencing reveals that the enzymes are conserved throughout evolution with greater than about 55% amino acid identity between human and bacterial proteins. A cDNA for human UDG has been cloned and the corresponding gene has been named UNG (Olsen et al. (1989) EMBO J., 8: 3121-3125).

The crystal structures of the human enzyme (Mol et al., (1995) Cell, 80: 869-878) and the herpes simplex virus enzymes (Savva et al. (1995) Nature, 373: 487-493) have recently been determined and reveal that uracil binds in a rigid pocket at the base of the DNA binding groove of human UDG. The absolute specificity of the enzyme for uracil over the structurally related DNA bases thymine and cytosine is conferred by shape complementarity, as well as main chain and side chain hydrogen bonds.

Although UDG's do not have activity against other bases as a result of the afore-mentioned specific spatial and charge characteristics of the active site, other glycosylases with different activities have been identified, which may or may not be restricted to single substrates.

A naturally-occurring thymine-DNA glycosylase has been identified which in addition to releasing thymine also releases uracil (Nedderman & Jiricny (1993) J. Biol. Chem., 268: 21218-21114; Nedderman & Jiricny (1994) J. Proc. Natl. Acad. Sci. U.S.A., 91: 1642-1646). This thymine-DNA glycosylase however has activity in respect of only certain substrates and has an absolute requirement for a mismatched U or T opposite of a G in a double-stranded substrate and will not recognise T or U from T(U):A matches or a single-stranded substrate. DNA glycosylases which recognize and release unmodified bases other than uracil and thymine (in certain substrates, as mentioned above) have not been identified.

A DNA glycosylase recognizing unmodified cytosine has not been reported, although a 5-hydroxymethylcytosine-DNA glycosylase activity was detected in mammalian cells (Cannon et al. (1988) Biochem. Biophys. Res. Comm., 151: 1173-1179). The sequences of the afore-mentioned thymine and 5-hydroxymethylcytosine DNA glycosylases have not yet been reported and it is unknown whether their active site may be structurally related to UDG.

It has now surprisingly been found that the substitution of certain of the UDG amino acids has a profound effect on the substrate specificity of the glycosylase. In particular, the replacement of Asn204 by Asp204 results in the production of a mutant enzyme which has acquired cytosine-DNA glycosylase (CDG) activity, while retaining some UDG-activity. Alternatively, replacing Tyr147 with Ala147 allows for binding of thymine, resulting in an enzyme that has acquired thymine-DNA glycosylase (TDG) activity.

These new DNA glycosylases are not product-inhibited by added uracil, in contrast to UDG and other UDG-mutants. Compared with the efficiency of wild type UDG in removal of uracil, the activity of the new DNA glycosylases that remove normal pyrimidines in DNA is low, but distinct and easily detectable. However, it should be noted that the very high turnover of UDG appears to be unique among DNA glycosylases and turnover numbers of other DNA glycosylases may be as low, or even lower than those of the engineered glycosylases CDG and TDG. This may result from the narrow substrate specificity of UDG.

Furthermore, an additional new UDG has been identified. The complete sequence of the UNG gene was recently published (Haug et al., 1996, Genomics, 36, p 408-416). As mentioned previously, cDNA to this UNG gene has been identified by Olsen et al., 1989, supra (hereinafter referred to as UNG1 cDNA and the expressed protein referred to as UNG1). It has now surprisingly been found that alternative splicing of the genomic DNA (UNG) with an exon located 5' of exon 1 which was not previously recognized results in a new distinct cDNA with an open reading frame of 313 amino acids. The new UNG cDNA is referred to hereinafter as UNG2 cDNA, and the product which it encodes, UNG2. The latter protein has a predicted size of 36 kDa.

UNG2 differs from the previously known form (UNG1, ORF 304 amino acid residues) in the 44 amino acids of the N-terminal presequence, which is not necessary for catalytic activity. The rest of the presequence and the catalytic domain, altogether 269 amino acids, are identical. The alternative presequence in UNG2 arises by splicing of a previously unrecognized exon (exon 1A) into a consensus splice site after codon 35 in exon 1B (previously designated exon 1). The UNG1 presequence starts at codon 1 in exon 1B and thus has 35 amino acids not present in UNG2. Coupled transcription/translation in rabbit reticulocyte lysates demonstrated that both proteins are catalytically active. Similar forms of UNG1 and UNG2 are expressed in mouse which has an identical organization of the homologous gene. Furthermore, the presequence of a putative *Xiphophorus* UNG2 protein predicted from the gene structure is homologous to mammalian UNG2, but much shorter, suggesting a very high degree of conservation from fish to man.

The invention therefore provides a DNA glycosylase capable of releasing cytosine bases from single stranded (ss) DNA and/or double stranded (ds) DNA or thymine bases from both single stranded (ss) DNA and double stranded (ds) DNA or from single stranded (ss) DNA or uracil bases from single stranded (ss) DNA and/or double stranded (ds) DNA, wherein said uracil-DNA glycosylase is encoded by a nucleic acid molecule comprising the sequence (SEQUENCE I.D. Nos 1 and 2):

```
   1 CACAGCCACA GCCAGGGCTA GCCTCGCCGG TTCCCGGGTG GCGCGCGTTC GCTGCCTCCT

61 CAGCTCCAGG ATGATCGGCC AGAAGACGCT CTACTCCTTT TTCTCCCCCA GCCCCGCCAG
                M   I   G   Q   K   T   L   Y   S   F   F   S   P   S   P   A

121 GAAGCGACAC GCCCCCAGCC CCGAGCCGGC CGTCCAGGGG ACCGGCGTGG CTGGGGTGCC
      R   K   R   H   A   P   S   P   E   P   A   V   Q   G   T   G   V   A   G   V

181 TGAGGAAAGC GGAGATGCGG CGGCCATCCC AGCCAAGAAG GCCCCGGCTG GGCAGGAGGA
      P   E   E   S   G   D   A   A   I   P   A   K   K   A   P   A   G   Q   E

241 GCCTGGGACG CCGCCCTCCT CGCCGCTGAG TGCCGAGCAG TTGGACCGGA TCCAGAGGAA
      E   P   G   T   P   P   S   S   P   L   S   A   E   Q   L   D   R   I   Q   R

301 CAAGGCCGCG GCCCTGCTCA GACTCGCGGC CCGCAACGTG CCCGTGGGCT TTGGAGAGAG
      N   K   A   A   A   L   L   R   L   A   A   R   N   V   P   V   G   F   G   E

361 CTGGAAGAAG CACCTCAGCG GGGAGTTCGG GAAACCGTAT TTTATCAAGC TAATGGGATT
      S   W   K   K   H   L   S   G   E   F   G   K   P   Y   F   I   K   L   M   G

421 TGTTGCAGAA GAAAGAAAGC ATTACACTGT TTATCCACCC CCACACCAAG TCTTCACCTG
      F   V   A   E   E   R   K   H   Y   T   V   Y   P   P   P   H   Q   V   F   T

481 GACCCAGATG TGTGACATAA AAGATGTGAA GGTTGTCATC CTGGGACAGG ATCCATATCA
      W   T   Q   M   C   D   I   K   D   V   K   V   V   I   L   G   Q   D   P   Y

541 TGGACCTAAT CAAGCTCACG GGCTCTGCTT TAGTGTTCAA AGGCCTGTTC CGCCTCCGCC
      H   G   P   N   Q   A   H   C   L   C   F   S   V   Q   R   P   V   P   P   P

601 CAGTTTGGAG AACATTIATA AAGAGTTGTC TACAGACATA GAGGATTTTG TTCATCCTGG
      P   S   L   E   N   I   Y   K   E   L   S   T   D   I   E   D   F   V   H   P

661 CCATGGAGAT TTATCTGGGT GGCCCAAGCA AGGTGTTCTC CTTCTCAACG CTGTCCTCAC
      C   H   G   D   L   S   G   W   A   K   Q   G   V   L   L   L   N   A   V   L

721 GGTTCGTGCC CATCAAGCCA ACTCTCATAA GGAGCGAGGC TGGGAGCAGT TCACTGATGC
      T   V   R   A   H   Q   A   N   S   H   K   E   R   C   W   E   Q   F   T   D

781 AGTTGTGTCC TGGCTAAATC AGAACTCGAA TGGCCTTGTT TTCTTGCTCT GGGGCTCTTA
      A   V   V   S   W   L   N   Q   N   S   N   C   L   V   F   L   L   W   C   S

841 TGCTCAGAAG AAGGGCAGTG CCATTGATAG GAAGCGGCAC CATGTACTAC AGACGGCTCA
      Y   A   Q   K   K   G   S   A   I   D   R   K   R   H   H   V   L   Q   T   A

901 TCCCTCCCCT TTGTCAGTGT ATAGAGGGTT CTTTGGATGT AGACACTTTT CAAAGACCAA
      H   P   S   P   L   S   V   Y   R   G   F   F   G   C   R   H   F   S   K   T

961 TGAGCTGCTG CAGAAGTCTG GCAAGAAGCC CATTGACTGG AAGGAGCTGT GATCATCAGC
      N   E   L   L   Q   K   S   G   K   K   P   I   D   W   K   E   L

1021 TGAGGGGTGG CCTTTGAGAA GCTGCTGTTA ACGTATTTGC CAGTTACGAA GTTCCACTGA

1081 AAATTTTCCT ATTAATTCTT AAGTACTCTG CATAAGGGGG AAAAGCTTCC AGAAAGCAGC

1141 CATGAACCAG GCTGTCCAGG AATGGCAGCT GTATCCAACC ACAAACAACA AAGGCTACCC

1201 TTTGACCAAA TGTCTTTCTC TGCAACATGG CTTCGGCCTA AAATATGCAG AAGACAGATG

1261 AGGTCAAATA CTCAGTTGGC TCTCTTTATC TCCCTTGCCT TTATGGTGAA ACAGGGGAGA

1321 TGTGCACCTT TCAGGCACAG CCCTAGTTTG GCGCCTGCTG CTCCTTGGTT TTGCCTGGTT

1381 AGACTTTCAG TGACAGATGT TGGGGTGTTT TTGCTTAGAA AGGTCCCCTT GTCTCAGCCT

1441 TGCAGGGCAG GCATGCCAGT CTCTGCCAGT TCCACTGCCC CCTTGATCTT TGAAGGAGTC

1501 CTCAGGCCCC TCGCAGCATA AGGATGTTTT GCAACTTTCC AGAATCTGGC CCAGAAATTA

1561 GGGCTCAATT TCCTGATTGT AGTAGAGGTT AAGATTGCTG TGAGCTTTAT CAGATAAGAG
```

```
-continued
1621 ACCGAGAGAA GTAAGCTGGG TCTTGTTATT CCTTGGGTGT TGGTGGAATA AGCAGTGGAA

1681 TTTGAACAAG GAAGAGGAGA AAAGGGAATT TTGTCTTTAT GGGGTGGGGT GATTTTCTCC

1741 TAGGGTTATG TCCAGTTGGG GTTTTTAAGG CAGCACAGAC TGCCAAGTAC TGTTTTTTTT

1801 AACCGACTGA AATCACTTTG GGATATTTTT TCCTGCAACA CTGGAAAGTT TTAGTTTTTT

1861 AAGAAGTACT CATGCAGATA TATATATATA TATTTTTCCC AGTCCTTTTT TTAAGAGACG

1921 GTCTTTATTG GGTCTGCACC TCCATCCTTG ATCTTGTTAG CAATGCTGTT TTTGCTGTTA

1981 GTCGGGTTAG AGTTGGCTCT ACGCGAGGTT TGTTAATAAA AGTTTGTTAA AAGTTCAAAA

2041 AAAAAAAAAA AAA
``` or a fragment thereof encoding a catalytically active product comprising at least nucleotides 121 to 130, preferably 71 to 202 in addition to the catalytic domain, or a sequence which is degenerate, substantially homologous with or which hybridizes with at least nucleotides 121 to 130, preferably 71 to 202 of any such aforesaid sequence.

In particular, viewed from one aspect, the invention can be seen as providing a cytosine-DNA glycosylase (CDG) capable of releasing cytosine bases from ssDNA and/or dsDNA.

A further aspect of the invention provides a cytosine-DNA glycosylase (CDG) capable of releasing both cytosine and uracil bases from ssDNA and/or dsDNA.

Preferably, the cytosine-DNA glycosylase is one derived from a UDG and especially from the human UDG protein which has Asn at amino acid position 204. In particular, the novel CDG of the invention is preferably derived from human UDG and has an amino acid substitution or modification at position 204. Modification of UDG from other species at an equivalent residue is similarly preferred. Especially preferably, the glycosylase is human UDG having an aspartic acid residue (Asp) at position 204.

Another aspect of the invention provides a thymine-DNA glycosylase (TDG) capable of releasing thymine bases from both ssDNA and dsDNA.

A further aspect of the invention provides a thymine-DNA glycosylase (TDG) capable of releasing both thymine and uracil bases from both ssDNA and dsDNA.

Yet further aspects of the invention provide a thymine-DNA glycosylase (TDG) capable of releasing thymine bases from A:T DNA pairs and a thymine-DNA glycosylase (TDG) capable of releasing thymine bases from single stranded DNA.

Preferably, the thymine-DNA glycosylase is one derived from a UDG, and especially from the human UDG protein which has Tyr at amino acid position 147. In particular, the novel CDG of the invention is preferably derived from human UDG and has an amino acid substitution or modification at position 147. Modification of UDG from other species at an equivalent residue is similarly preferred. Especially preferably, the glycosylase is human UDG having a alanine residue (Ala) at position 147.

A yet further aspect of the invention provides a uracil-DNA glycosylase encoded by a nucleic acid molecule comprising the sequence (SEQUENCE I.D Nos 1 and 2):

```
  1 CACAGCCACA GCCAGGGCTA GCCTCGCCGG TTCCCGGGTG GCGCGCGTTC GCTGCCTCCT

61 CAGCTCCAGG ATGATCGGCC AGAAGACGCT CTACTCCTTT TTCTCCCCCA GCCCCGCCAG
              M   I   G   Q   K   T   L   Y   S   F   F   S   P   S   P   A

121 GAAGCGACAC GCCCCCAGCC CCGAGCCGGC CGTCCAGGGG ACCGGCGTGG CTGGGGTGCC
     R   K   R   H   A   P   S   P   E   P   A   V   Q   G   T   G   V   A   G   V

181 TGAGGAAAGC GGAGATGCGG CGGCCATCCC AGCCAAGAAG GCCCCGGCTG GGCAGGAGGA
     P   E   E   S   G   D   A   A   I   P   A   K   K   A   P   A   G   Q   E

241 GCCTGGGACG CCGCCCTCCT CGCCGCTGAG TGCCGAGCAG TTGGACCGGA TCCAGAGGAA
     E   P   G   T   P   P   S   S   P   L   S   A   E   Q   L   D   R   I   Q   R

301 CAAGGCCGCG GCCCTGCTCA GACTCGCGGC CCGCAACGTG CCCGTGGGCT TTGGAGAGAG
     N   K   A   A   A   L   L   R   L   A   A   R   N   V   P   V   G   F   G   E

361 CTGGAAGAAG CACCTCAGCG GGGAGTTCGG GAAACCGTAT TTTATCAAGC TAATGGGATT
     S   W   K   K   H   L   S   G   E   F   G   K   P   Y   F   I   K   L   M   G

421 TGTTGCAGAA GAAAGAAAGC ATTACACTGT TTATCCACCC CCACACCAAG TCTTCACCTG
     F   V   A   E   E   R   K   H   Y   T   V   Y   P   P   P   H   Q   V   F   T

481 GACCCAGATG TGTGACATAA AAGATGTGAA GGTTGTCATC CTGGGACAGG ATCCATATCA
     W   T   Q   M   C   D   I   K   D   V   K   V   V   I   L   G   Q   D   P   Y

541 TGGACCTAAT CAAGCTCACG GGCTCTGCTT TAGTGTTCAA AGGCCTGTTC CGCCTCCGCC
     H   G   P   N   Q   A   H   C   L   C   F   S   V   Q   R   P   V   P   P   P

601 CAGTTTGGAG AACATTTATA AAGAGTTGTC TACAGACATA GAGGATTTTG TTCATCCTGG
```

```
                P   S   L   E       N   I   Y       K   E   L       S   T   D   I       E   D   F       V   H   P
       661 CCATGGAGAT TTATCTGGGT GGGCCAAGCA AGGTGTTCTC CTTCTCAACG CTGTCCTCAC
                C   H   G   D       L   S   G       W   A   K       Q   G   V   L       L   L   N       A   V   L

721 GGTTCGTGCC CATCAAGCCA ACTCTCATAA GGAGCGAGGC TGGGAGCAGT TCACTGATGC
                T   V   R   A       H   Q   A       N   S   H       K   E   R   G       W   E   Q       F   T   D

781 AGTTGTGTCC TGGCTAAATC AGAACTCGAA TGGCCTTGTT TTCTTGCTCT GGGGCTCTTA
                A   V   V   S       W   L   N       Q   N   S       N   C   L   V       F   L   L       W   C   S

841 TGCTCAGAAG AAGGGCAGTG CCATTGATAG GAAGCGGCAC CATGTACTAC AGACGGCTCA
                Y   A   Q   K       K   G   S       A   I   D       R   K   R   H       H   V   L       Q   T   A

901 TCCCTCCCCT TGTCAGTGT  ATAGAGGGTT CTTTGGATGT AGACACTTTT CAAAGACCAA
                H   P   S   P       L   S   V       Y   R   G       F   F   G   C       R   H   F       S   K   T

961 TGAGCTGCTG CAGAAGTCTG GCAAGAAGCC CATTGACTGG AAGGAGCTGT GATCATCAGC
                N   E   L   L       Q   K   S       G   K   K       P   I   D   W       K   E   L

1021 TGAGGGGTGG CCTTTGAGAA GCTGCTGTTA ACGTATTTGC CAGTTACGAA GTTCCACTGA

1081 AAATTTTCCT ATTAATTCTT AAGTACTCTG CATAAGGGGG AAAAGCTTCC AGAAAGCAGC

1141 CATGAACCAG GCTGTCCAGG AATGGCAGCT GTATCCAACC ACAAACAACA AAGGCTACCC

1201 TTTGACCAAA TGTCTTTCTC TGCAACATGG CTTCGGCCTA AAATATGCAG AAGACAGATG

1261 AGGTCAAATA CTCAGTTGGC TCTCTTTATC TCCCTTGCCT TTATGGTGAA ACAGGGGAGA

1321 TGTGCACCTT TCAGGCACAG CCCTAGTTTG GCGCCTGCTG CTCCTTGGTT TTGCCTGGTT

1381 AGACTTTCAG TGACAGATGT TGGGGTGTTT TTGCTTAGAA AGGTCCCCTT GTCTCAGCCT

1441 TGCAGGGCAG GCATGCCAGT CTCTGCCAGT TCCACTGCCC CCTTGATCTT TGAAGGAGTC

1501 CTCAGGCCCC TCGCAGCATA AGGATGTTTT GCAACTTTCC AGAATCTGGC CCAGAAATTA

1561 GGGCTCAATT TCCTGATTGT AGTAGAGGTT AAGATTGCTG TGAGCTTTAT CAGATAAGAG

1621 ACCGAGAGAA GTAAGCTGGG TCTTGTTATT CCTTGGGTGT TGGTGGAATA AGCAGTGGAA

1681 TTTGAACAAG GAAGAGGAGA AAAGGGAATT TTGTCTTTAT GGGGTGGGGT GATTTTCTCC

1741 TAGGGTTATG TCCAGTTGGG GTTTTTAAGG CAGCACAGAC TGCCAAGTAC TGTTTTTTTT

1801 AACCGACTGA AATCACTTTG GGATATTTTT TCCTGCAACA CTGGAAAGTT TTAGTTTTTT

1861 AAGAAGTACT CATGCAGATA TATATATATA TATTTTTCCC AGTCCTTTTT TTAAGAGACG

1921 GTCTTTATTG GGTCTGCACC TCCATCCTTG ATCTTGTTAG CAATGCTGTT TTTGCTGTTA

1981 GTCGGGTTAG AGTTGGCTCT ACGCGAGGTT TGTTAATAAA AGTTTGTTAA AAGTTCAAAA

2041 AAAAAAAAAA AAA
``` or a fragment thereof encoding a catalytically active product comprising at least nucleotides 121 to 130, preferably 71 to 202 in addition to the catalytic domain, or a sequence which is degenerate, substantially homologous with or which hybridizes with at least nucleotides 121 to 130, preferably 71 to 202 of any such aforesaid sequence. Preferably such degeneracy, homology or hybridization applies to the entire sequence.

"Catalytically active product" as used herein refers to any product encoded by said sequence which exhibits uracil DNA glycosylase activity.

"Substantially homologous" as used herein includes those sequences having a sequence homology of approximately 60% or more, eg. 70% or 80% or more, and also functionally-equivalent allelic variants and related sequences modified by single or multiple base substitution, addition and/or deletion. By "functionally equivalent" in this sense is meant nucleotide sequences which encode catalytically active polypeptides, ie. having uracil DNA glycosylase activity.

Sequences which "hybridize" are those sequences binding under non-stringent conditions (eg. 6×SSC 50% formamide at room temperature) and washed under conditions of low stringency (eg. 2×SSC, room temperature, more preferably 2×SSC, 42° C.) or conditions of higher stringency (eg. 2×SSC, 65° C.) (where SSC=0.15M NaCl, 0.015M sodium citrate, pH 7.2). Generally speaking, sequences which hybridize under conditions of high stringency are included within the scope of the invention, as are sequences which, but for the degeneracy of the code, would hybridize under high stringency conditions.

The significance of the UNG1, UNG2 presequences has also been investigated in the present invention, by the use of constructs that express fusion products of UNG1 or UNG2 and green fluorescent protein (EGFP). Surprisingly, significant effects on subcellular targeting were observed and after transient transfection of HeLa cells, the pUNG1-EGFP-N1 product co-localized with mitochondria whereas the pUNG2-EGFP-N1 product targeted exclusively to nuclei. Whilst not wishing to be bound by theory, it appears that these sequences may be instrumental in the localization of the enzymes. The putative nuclear signal was identified as RKRH which also appears in the catalytic domain of both UNG1 and UNG2. Whilst it was recognized previously by Slupphaug et al., 1993, Nucl. Acids Res., 21(11), p 2579-2584, that the signal for mitochondrial translocation resides in the UNG1 presequence, it was believed that the signal for nuclear import lay within the mature protein as in the absence of the presequence, UNG1 was transported to the nucleus. However, UNG2 has now been identified which has a presequence and which localizes to the nucleus. These presequences thus have utility for directing the subcellular localization of molecules attached to them.

Thus, viewed from a further aspect, the invention provides nuclear localization peptides encoded by a nucleic acid molecule comprising the sequence (SEQUENCE I.D. Nos 3 and 4):

```
ATGATCGGCC AGAAGACGCT CTACTCCTTT TTCTCCCCCA GCCCCGCCAG
  M   I  G   Q  K  T    L  Y  S  F    F  S  P  S  P    S  P  A

GAAGCGACAC GCCCCCAGCC CCGAGCCGGC CGTCCAGGGG ACCGGCGTGG CTGGGGTGCC
 R  K  R  H   A  P  S    P  E  P    A  V  Q  G    T  G  V    A  G  V

TGAGGAAAGC GGAGATGCGG CG
 P  E  E  S    G  D  A    A
``` or a fragment thereof encoding a functional equivalent or a sequence which is degenerate, substantially homologous with or which hybridizes with any such aforesaid sequence.

Functionally equivalent fragments refer to products which may serve as appropriate localization peptides. Especially preferred nuclear localizing peptides are those which include the amino acid sequence RKRH.

A further preferred feature of the invention comprises DNA glycosylases of the invention which additionally comprise at least one of the aforesaid nuclear localization peptide sequences or at least one mitochondrial localization peptide sequence encoded by a nucleic acid molecule comprising the sequence (SEQUENCE I.D. Nos 5 and 6):

```
ATGGGCGTCT TCTGCCTTGG GCCGTGGGGG TTGGGCCGGA AGCTGCGGAC GCCTGGGAAG
  M  G   V    F  C  L    G  P  W  G    L  G  R    K  L  R    T  P  G  K

GGGCCGCTGC AGCTCTTGAG CCGCCTCTGC GGGGACCACT TGCAG
  G  P  L    Q  L  L    S  R  L  C    G  D  H    L  Q
``` or a fragment thereof encoding a functional equivalent or a sequence which is degenerate, substantially homologous with or which hybridizes with any such aforesaid sequence, e.g. CDG or TDG with a localization peptide. Such a composite may be prepared for example by appropriate modification of UNG1 or UNG2.

The novel DNA glycosylases of the invention conveniently may be obtained by modification of existing DNA glycosylase enzymes, such as the human UDG mentioned above. Such modification, for example by replacement, addition or deletion of one or more amino acid residues, or indeed chemical modification of amino acid residues, may readily be achieved using methods well known in the art and include modifications both at the protein level and also at the level of the encoding nucleic acid. For example, site-directed mutagenesis techniques are widely described in the literature. Other conventional mutagenesis treatments which may be used to obtain enzymes according to the invention include random or regional random mutagenesis by chemical agents, such as N-nitroso compounds, or physical agents, such as ultraviolet light, as well as random or regional random mutagenesis by polymerase chain reaction (PCR) methods. Regional random mutagenesis may be carried out by subcloning one or more relevant DNA sequences encoding segments of the starting protein e.g. UDG, followed by random mutagenesis on this fragment or fragments. After the fragments have been mutagenized they may be reinserted into a DNA sequence encoding the starting protein e.g. UDG. Screening of individual colonies for novel DNA glycosylases of the invention may then be performed using assay methods described herein.

Alternatively, the novel DNA glycosylases of the invention may be obtained by other techniques, for example polypeptide synthesis, construction of fusion proteins etc.

DNA glycosylase activity may readily be assayed according to techniques well known in the art, see for example Slupphaug et al. (1995) Biochemistry, 34: 128-138, and Nedderman & Jiricny, supra. Assays for DNA glycosylase may be used for identifying enzymes according to the invention. The enzymes may be naturally occurring or formed as the result of manipulations of naturally occurring gene sequences or products. Thus, for example, a cell-free extract may be assayed using a thymine or cytosine-containing substrate to identify enzymes which perform excision of one or more of the bases. For the purposes of assessment, the cytosine and thymine bases in the substrates are conveniently labelled, for example fluorescent or radiolabelled e.g. with $^3$H. Suitable substrates may be prepared by methods known in the art e.g. by nick translation, random priming, PCR or chemical synthesis. To ascertain if the enzymes are also capable of excising uracil, substrates including uracil may also be used. Conveniently, the uracil bases should be labelled to allow detection. Assays for the excision of different bases are preferably performed independently.

Thus, viewed from a yet further aspect, the invention provides an assay for the identification of DNA glycosylases of the invention in a sample, in which said assay comprises at least the step of assaying for activity in the sample which is capable of excising thymine or cytosine and optionally also uracil from an introduced ssDNA and/or dsDNA substrate. Optionally, the moiety responsible for such activity may be isolated. Suitable assays are described herein and are also known in the art.

DNA glycosylases of the invention include modifications of human UDG by amino acid replacement, as mentioned above, especially at positions 204 and 147. Such amino acid-substituted mutants of human UDG may also comprise additional modifications, for example truncation from the N- and/or C-terminal, or chemical derivation of amino acid residues and/or addition, deletion or mutation of constituent residues which do not affect the overall specificity of the enzyme.

Derivatives of UDG or other DNA glycosylase enzymes from other genera or species, having the CDG or TDG functional activity mentioned above, are also included within the scope of the invention. It will be appreciated that appropriate modification of such enzymes would be performed on comparable residues to those in the human enzyme which form part of the active site and which could be identified by methods known in the art, e.g. by sequence comparison to human UDG and/or by mutation of residues which are identified as potentially conferring specificity to the enzyme and subsequent substrate specificity analyses of the mutant enzymes thus obtained.

The novel DNA glycosylases of the invention may have a number of uses, for example as tools in molecular biology procedures, most notably in mutagenesis, both in vitro and in vivo, but also in other areas such as cell killing, removal of contaminating DNA, random degradation of DNA, enzymatic DNA sequencing etc.

In light of the identification of mitochondrial and nuclear localizing peptides, it is now possible to direct human uracil-DNA glycosylase either to nuclei or to mitochondria by making constructs containing either a nuclear localization signal, such as in UNG2, or a mitochondrial localization signal, such as in UNG1, as mentioned above. Whilst this alone may be used to mutate RNA in the cells, this is particularly useful in combination with site directed mutations that give rise to mutants that have either TDG activity or CDG activity because it allows for selective mutagenesis of nuclear DNA or mitochondrial DNA. Furthermore, it is useful in a system where either nuclear or mitochondrial DNA is the target for degradation for the purpose of killing cells, eg. cancer cells.

As mentioned above, DNA glycosylases according to the invention may be used in a mutagenesis system both in vitro and in vivo. These proteins have numerous advantages over typical chemical mutagens, particularly regarding their ease of use. Small molecular mutagens, such as methylnitrosurea (MNU), methylmethanesulfonate (MMS) or methylnitrosoguanidine (MNNG) are very toxic on contact with eyes, skin or mucosal membranes and may decompose to explosive and volatile toxic compounds. Other mutagens, such as dimethylnitrosamine and benzo(a)pyrene require metabolic activation by special enzymes that are only present in some cells. They can therefore only be used under certain experimental conditions and will often require the addition of a fraction containing activating enzymes. All these chemical mutagens therefore require specialised precautions in order to protect the user. One major advantage of DNA glycosylases according to the invention is that they are not volatile and are not harmful to the user, for example, by mere skin contact.

Mutagenesis in vitro may be performed on a complex sample, e.g. a cell-free extract, a partially refined sample, e.g. nucleic-acid enriched or purified sample or on a single population of nucleic acid material, e.g. amplified nucleic acid material. Random mutation may be performed using selected DNA glycosylases of the invention (possibly in combination with one another and/or with known DNA glycosylases), to release particular bases or combinations of bases from the nucleic acid substrate. Removal of the resulting abasic site and replacement of the removed base with another base may be performed by provision of appropriate enzymes and bases.

Specific mutagenesis may be performed in a number of ways. Depending on the specificity of the DNA glycosylase for ssDNA or dsDNA, either one or the other type of DNA may be targeted. One application of such a method may be to introduce labelled bases into the target DNA to identify its presence or amount in the total nucleic acid material. Alternatively, the substrate which is uniquely recognizable (e.g. dsDNA) may be made sensitive to digestion or degradation after release of the appropriate base by DNA glycosylase activity when replacement of the base has not been performed. This may then be used to remove certain ss- or ds-DNA from a sample. Such an application is discussed in more detail hereinafter.

Another application involves the introduction of selected bases after release of the specific bases recognized by the DNA glycosylase. In this way, replacement of specific bases by specific other bases may be performed. It is known from the art that the human UDG has sequence specificity for uracil excision in the sequence surrounding the uracil base (Slupphaug et al., 1995, supra). Appropriate selection of enzyme concentrations and other determinants may be employed to excise specific bases from known sequences or alternatively, by replacement with appropriately labelled bases, to determine the presence of such sequences in nucleic acid samples.

For mutagenesis in vivo, e.g. in a cell, a nucleotide sequence encoding a DNA glycosylase according to the invention under the control of an suitable expression vector may be introduced into the cell by any suitable means, for example, by transformation or through the use of liposomes.

A further aspect of the present invention thus provides a nucleic acid molecule comprising a nucleotide sequence which encodes a DNA glycosylase and/or nuclear localizing peptide of the invention as defined above. Such nucleic acid molecules may readily be prepared using conventional techniques well known in the art. Thus, for example, as already mentioned above, known gene sequences coding for DNA glycosylases, e.g. the UNG gene mentioned above, may be modified e.g. by nucleic acid substitution using standard techniques such as site-directed mutagenesis.

In further aspects the invention also provides an expression vector containing a nucleic acid molecule of the invention, and transformed or transfected host cells carrying a nucleic acid molecule of the invention.

The expression vector may be any conventional expression vector known in the art or described in the literature, including both phage and plasmid vectors. In general, these will comprise suitable regulatory sequences e.g. a promoter and/or enhancer operably connected to a gene expressing the enzyme. Suitable promoters include SV40 early or late promoter, e.g. PSVL vector, cytomegalovirus (CMV) promoter and mouse mammary tumour virus long terminal repeat, although preferably inducible promoters are used, e.g. mouse metallothionein I promoter. The vector preferably includes a suitable marker such as a gene for dihydrofolate reductase or glutamine synthetase. The expression vector may for example be an inducible vector, such as the E. Coli vector pTrc99A (See Slupphaug (supra)) inducible with isopropyl β-D-thiogalactopyranoside (IPTG). Other suitable expression vectors include any vector carrying an inducible promoter, such as lac, or bacteriophage lambda λ $P_L$, in which the promoter is under the control of a temperature sensitive repressor (cI). Examples of such vectors are pKK223-2 and $pP_L$-Lambda Inducible (from Pharmacia). The DNA glycosylases of the invention may also be expressed as fusion proteins. The expression of such fusion proteins may facilitate purification e.g. by using a system such as the GST-gene fusion systems, exemplified by the pGEX vector systems (Pharmacia) or the fusion proteins with peptide sequences that are recognized by specific antibodies, exemplified by the FLAG Expression vectors (Kodak).

The host cell may likewise be any suitable host cell known in the art, including both eukaryotic e.g. yeast, mammalian and plant cells, and prokaryotic cells, e.g. bacteria.

Transfection and transformation techniques are also well known in the art as described for example in Sambrook et al. (1989), Molecular Cloning: A laboratory manual, 2nd Ed., Cold Spring Harbor Laboratory Press, Cold Spring harbor, N.Y.) as indeed are other techniques for introducing nucleic acids into cells, for example using calcium phosphate, DEAE dextran, polybrene, protoplast fusion, liposomes electroporation, direct microinjection, gene cannon etc.

Expression of the DNA glycosylase according to the invention results in the release of C or T from the cellular DNA, which may lead to transition mutations upon replication.

Mutagenesis of cells, e.g. mammalian cells, may also be performed by introduction of the DNA glycosylase protein of the invention into the cell. This may be performed using for example liposomes or other appropriate techniques known in the art.

TDG or CDG may also be used to specifically induce mutations either in the cell nucleus or mitochondria of eukaryotic cells. This may be carried out by expressing cDNA with the complete open reading frame of UNG2, but with a site directed mutation in codon 204 (preferably Asn204Asp) or in codon 147 (preferably Tyr147Ala), in which the N-terminal amino acid sequence contains a nuclear localization signal, as described previously, to obtain mutations in the nuclear DNA, or by expressing a cDNA expressing the complete reading frame of UNG1, in which the N-terminal amino acid sequence contains a mitochondrial localization signal, as described previously, with similar site directed mutations to those mentioned above, to specifically obtain mitochondrial mutations. For this purpose any expression vector applicable to eukaryotic cells may be used, but preferably the vector system should be inducible. To introduce the expression vectors into the cells, any method for transfection my be used. Alternatively, the same proteins may be expressed and purified and then introduced into the cells by liposome technology or other appropriate techniques in the art as mentioned previously.

Combined in vitro/in vivo mutagenesis may also be performed. For example, an isolated restriction fragment of interest (or possibly the whole plasmid) may be treated with limited amounts of cytosine-DNA glycosylase or thymine-DNA glycosylase. Subsequently, the treated fragment may be reinserted into a vector and transformed into E. coli cells (the cells may also be pre-treated with a DNA damaging agent to ensure an error-prone SOS-repair). As a result of the mutagenicity of AP-sites, this should yield random mutations.

The Examples below describe the induction of mutations in bacterial cells by the expression within such cells of a DNA glycosylase ie. a CDG or TDG according to the present invention. Expression of the DNA glycosylases of the invention in the transformed cells causes an increase in mutation frequencies. Similar results may be obtained with other cells. To enhance mutagenesis, strains may be used, including both prokaryotic and eukaryotic strains, which are defective in the repair of AP-sites or are otherwise hypermutatable e.g. bacterial mutants that are defective in endonuclease IV or exonuclease III, or both, or other mutants that similarly enhance the yield of mutations.

Thus, the use of one or more DNA glycosylases according to the invention in in vitro and/or in vivo mutagenesis systems provide yet further aspects of this invention.

Another use of DNA glycosylases of the invention involves DNA modification. By treating any type of DNA (single or double-stranded) in vitro with a DNA glycosylase according to the invention, naturally-occurring C or T will be released, thus leaving an apyrimidic site (AP-site). Subsequent treatment of this DNA with alkaline solutions or enzymes such as apurinic/apyrimidinic-site endonucleases (AP-endonucleases) recognising AP-sites will cause breaks in the DNA at the AP-sites. This method may therefore be used for the random cleavage of DNA. The number of cleaved sites will depend on the amount of the DNA glycosylases according to the invention used, thus allowing the number of AP-sites and hence breaks to be controlled. Uses of such methods include the removal of possible contaminating DNA prior to PCR amplification and for the enzymatic sequencing of DNA. The random cleavage of DNA can also be used for producing randomly fragmented DNA of defined size ranges for different purposes, for example for efficient hybridization of DNA, for preparing genomic libraries or for removal of high-molecular weight viscous DNA.

One advantage of using a DNA glycosylase according to the invention in such methods is that in contrast to nucleates, DNA glycosylases do not require divalent cations and this is advantageous when buffers containing divalent cations are not desirable. A further advantage is that the DNA glycosylase may be inactivated by heating the reaction mixture to 80° C. for 15 minutes, thus eliminating or substantially reducing its activity.

Uracil-DNA glycosylase has previously been shown to be efficient in removing contaminating DNA prior to PCR amplification. This method has the disadvantage that only DNA containing uracil could be removed and meant that uracil-containing DNA had to be prepared using appropriate uracil-containing primers to obtain DNA which could be removed prior to amplification. One advantage of the DNA glycosylases according to the present invention is that they do not have this requirement as any contaminating DNA would be likely to contain cytosine or thymine bases. Thus, CDG and/or TDG according to the invention may be added to a reaction mix and allowed to digest contaminating DNA. After treatment the enzymes/s are inactivated prior to the addition of the DNA sample and amplification to avoid is degradation of the template or product.

Thus a further aspect of the invention provides the use of one of more DNA glycosylases according to the present invention for removing contaminating DNA prior to PCR amplification. The use of one or more DNA glycosylases according to invention in DNA modification provides a further aspect of the invention. The term "modification" as used herein refers to all forms of modifying or manipulating DNA, including cleavage, base substitution or insertion etc.

A DNA glycosylase according to the present invention may also be used in a method for the killing of cells. A DNA glycosylase according to the present invention may be introduced into specific target cells by means of known transformation techniques, liposomes, specific targeting systems such as ligands that bind to specific receptors, or any other suitable techniques. The DNA glycosylase may be expressed in a tissue-specific manner by placing a tissue-specific promoter upstream of the DNA sequence encoding a DNA glycosylase according to the present invention. Examples of such tissue-specific promoters are well known and are for example found in genes for a number of liver specific proteins such as albumin, blood clotting factors and apolipoproteins; several hormones, such as human growth hormone from the pituitary gland and insulin from Langerhans islands in pancreas, as well as aromatase involved in the estrogen biosynthetic pathway; porphobilinogen deaminase which is the third enzyme in the heme biosynthetic pathway; glycoprotein IIb/IIIa which is expressed in maturing megakaryocytes; the Zeta subunit of T-cell antigen receptor (TCR) which is expressed in T-cells; CD14 expressed in monocytes and macrophages; villin expressed in certain epithelial tissues and tyrosinase expressed in melanocytes and melanomas. In some cases abnormal expression from tissue specific promoters has been observed in tumour cells, and this may be exploited by using constructs of novel DNA glycosylases and the relevant tissue specific promoter.

When the DNA glycosylase is expressed it may fragment the DNA in the cell and therefore kill the cell. Specific cells may also be targeted through the use of promoters containing other control elements, for example, promoters which are controlled in a cell-cycle or temporal manner or those possessing regulatory elements responsive to internal or external factors, e.g. promoters activatable by specific inducers, e.g. the inducer IPTG, which induces the lac promoter or lac derivatives such as trc, by certain metals (e.g. metallothionein promoter), by certain hormones such as dexamethasone, androgens (on for example the promoter of the gene for prostate specific antigen which is tissue specific), retinic acid and certain cytokines.

Conceivably, where enzymes of the invention exhibit specific substrate requirements in the sequence surrounding the base for excision, this specificity may be employed by appropriate low level expression of the DNA glycosylase such that only DNA with the specific sequence is made susceptible to degradation.

Thus a further aspect of the invention provides a method of killing cells, comprising the steps of introducing a DNA glycosylase according to the present invention into a cell and expressing said DNA glycosylase in the cell to an extent which results in the killing of that cell. Preferably, the DNA glycosylase according to the present invention is contained within an expression vector, most preferably, a tissue-specific expression vector.

A further use of DNA glycosylases of the invention is for performing enzymatic DNA sequencing. This may be performed in a manner analogous to the chemical sequencing method of Maxam and Gilbert (Maxam and Gilbert (1980) Methods in Enzymology, 65: 499). However, the Maxam-Gilbert procedure involves the use of several very toxic chemicals, such as dimethylsulfate (DMA) and hydrazine (the latter is also explosive) and use of the glycosylases of the invention present a considerable advantage. Enzymatic sequencing may be performed for example by end-labelling the sample DNA fragment appropriately, for example with $^{32}P$, $^{33}P$ or $^{35}S$. For identifying the positions of cytosines and thymines in the DNA, the DNA is treated with limiting amounts of cytosine-DNA glycosylase and thymine-DNA glycosylase according to the invention, respectively. The resulting AP-sites are then cleaved, e.g. by alkaline solution (pyridine) or by an AP-endonuclease. The resulting end-labelled fragments are subsequently separated e.g. by electrophoresis and the position of fragments of varying length identified appropriately, e.g. by autoradiography. Ideally, the positions of adenines and guanines should be determined in the same way using adenine- or guanine-DNA glycosylases. At the present time such enzymes are not available. However, the E. coli DNA repair enzymes Tag and AlkA recognize adenine alkylated in the 3-position (Tag, AlkA) and guanine alkylated in the 3-position (AlkA). Thus, one way of determining the positions of adenines and guanines may be after alkylation of DNA with DMS, followed by treatment with AlkA and Tag. Subsequent experimental procedure may be performed as for determining the C and T positions.

Thus, a further aspect of the invention provides a method of performing enzymatic DNA sequencing to determine the position of cytosine and/or thymine bases by treating said DNA with at least one CDG and/or TDG of the invention.

Figure 2:
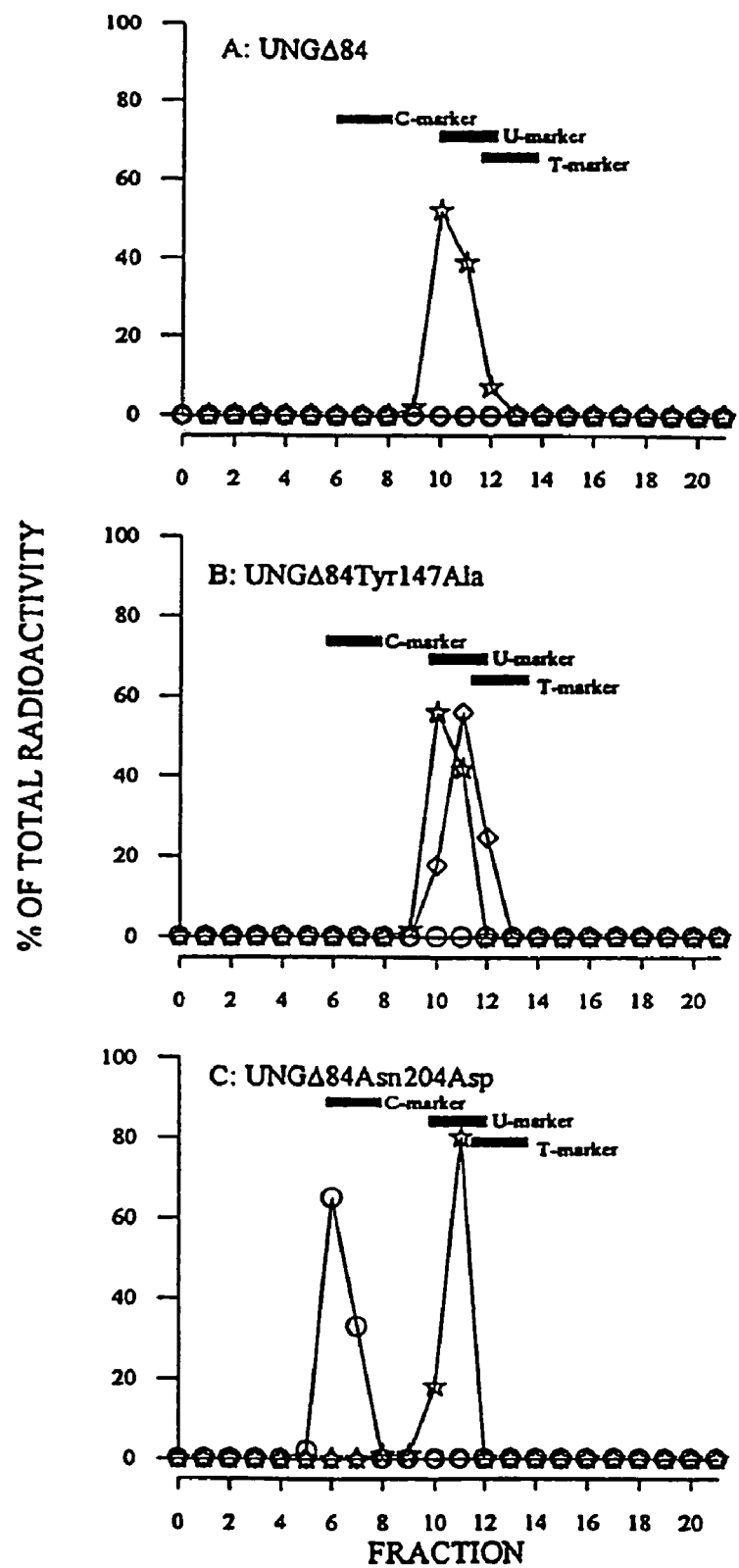
Figure 3:
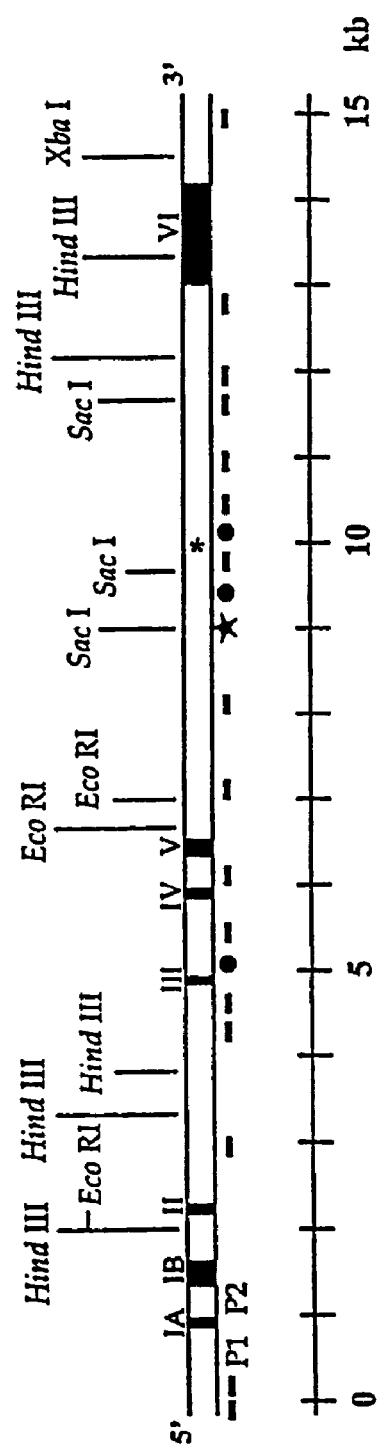
Figure 4:
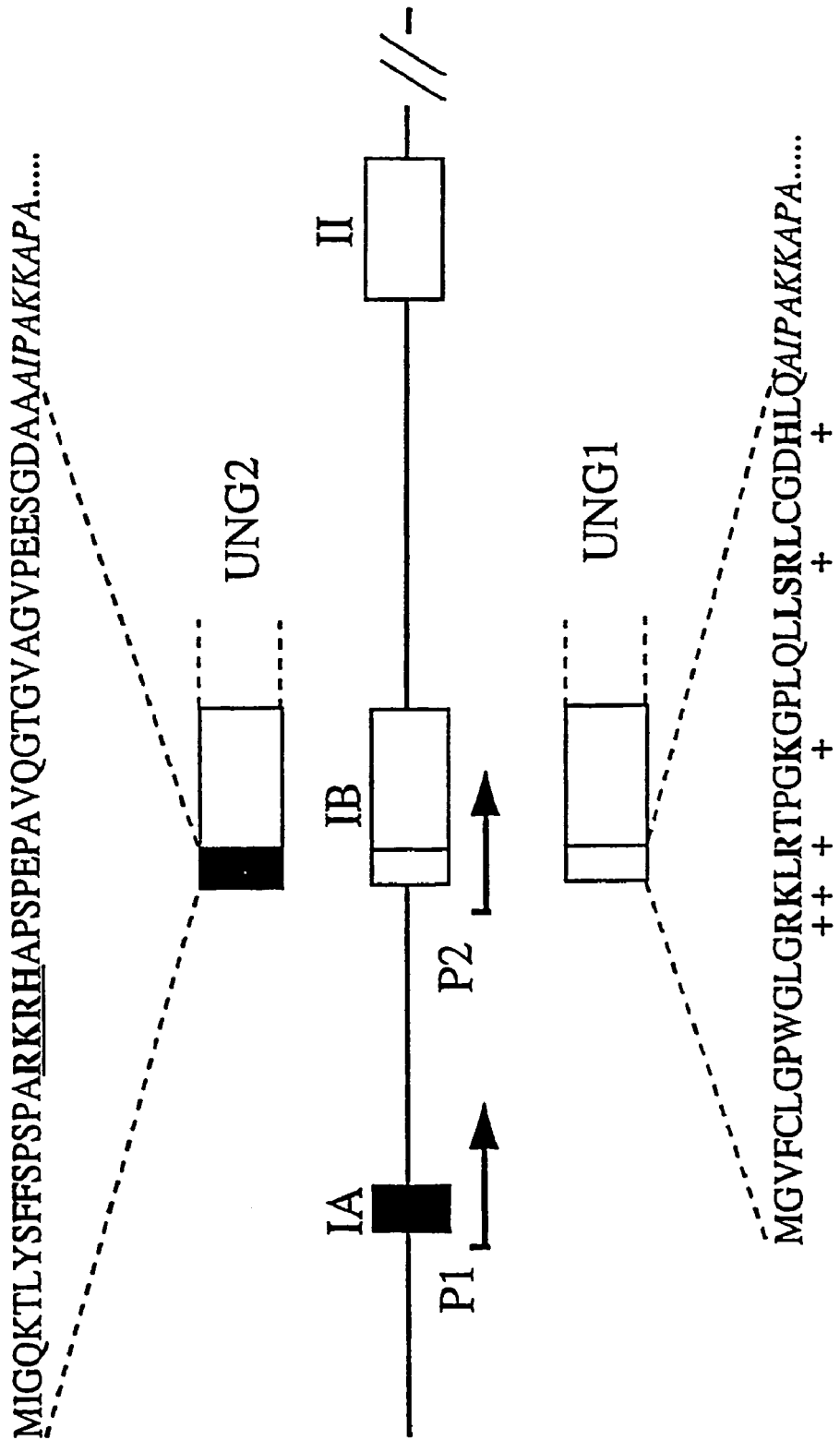
Figure 7:
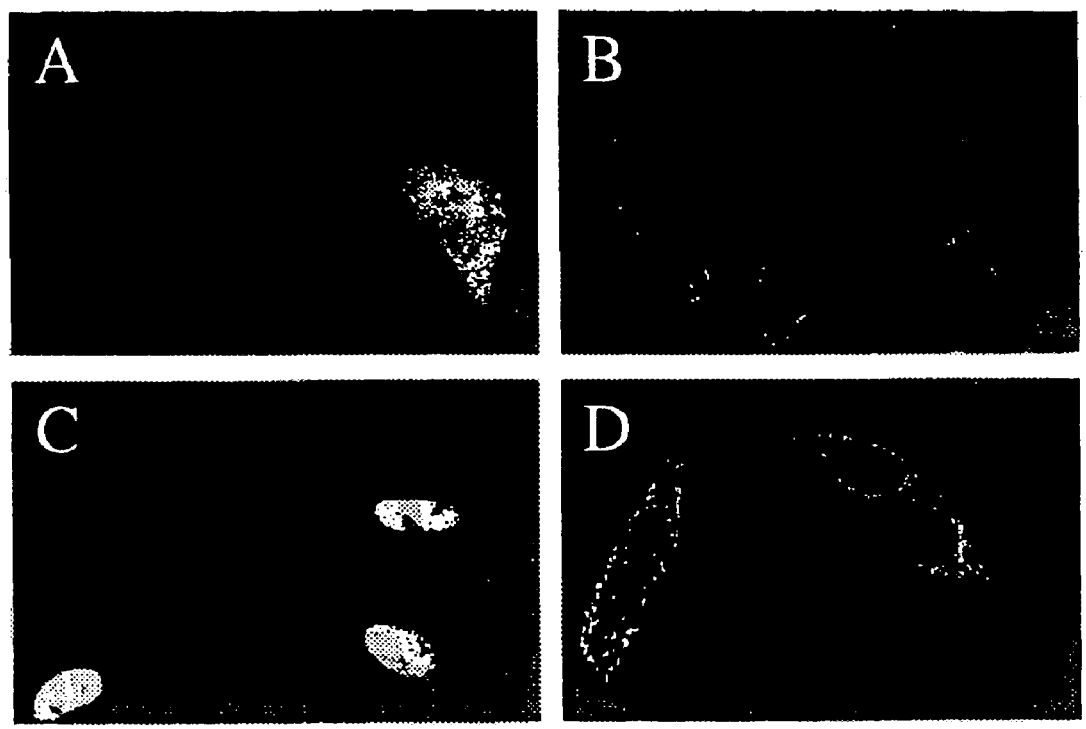

The invention will now be described more specifically in the following non-limiting Examples with reference to the following drawings in which:

FIG. 1 comprises graphs showing in vitro excision of radio-labelled material from double stranded (ds) or single stranded (ss) [$^{3}$H]cytosine-labelled DNA substrate (C-substrate) and [$^{3}$H]thymine-labelled DNA substrate (T-substrate) by human UDG-mutants (CDG: Panel A, TDG: Panel B). The data represent mean values from two independent experiments each in duplicate for each time point. Symbols in panel B of FIG. 1 are as indicated in panel A;

FIG. 2 comprises graphs showing analysis of the radioactive excision products of substrate DNA by UDG (panel A) and UDG mutants TDG (Panel B) and CDG (Panel C), performed by thin layer chromatography. U-substrate is indicated by stars (☆), other symbols are as in FIG. 1. The migration of unlabelled standards (the free bases uracil, cytosine or thymine) is indicated as rectangles, marked respectively U-marker, C-marker and T-marker over the relevant fraction numbers;

FIG. 3 shows a revised organisation of the human UNG gene. The restriction maps with EcoRI, HindIII, SacI and XbaI are indicated. Exons are shown as black boxes and are numbered by Roman numbers. Exon 1A is a previously unrecognised exon. Interspersed repeats are indicated (−: Alu, •: MER, ♦: MIR, *: position of a 300 bp TA dinucleotide repeat);

FIG. 4 shows the generation of human UNG1 and UNG2 by transcription from two promoters and alternative splicing. P2 is the previously recognised promoter for transcription of UNG1 (Haug et al., 1994, FEBS Letters, 353, p 180-184) and P1 the promoter from which UNG2 is transcribed. Exon 1A encodes 44 amino acids present in UNG2, but absent in UNG1. The 35 N-terminal codons of exon 1B are only present in UNG1. The presequence of UNG2 is shown on top with the putative nuclear localization signal underlined. The presequence of UNG1 directing mitochondrial import is shown in the bottom line;

FIG. 5 shows the structure of the 5'-terminal part of the human UNG gene (SEQUENCE I.D. No. 7). Bold letters indicate exons (1A and 1B);

FIG. 6 shows the alignment of UNG proteins from man and mouse (SEQUENCE ID Nos 8 (hUNG1), 9 (mUNG1), 2 (hUNG2) and 10 (mUNG2)). Note that UNG1 and UNG2 proteins have been aligned separately down to the common splice corresponding to codon 44 in human UNG2. The presequence not present in the catalytically active form of human placental uracil-DNA glycosylase originally isolated, residues 1-77 in human UNG1 (Wittwer et al., 1989, Biochemistry, 28, p 780-784) is shown in bold letters. Downstream of the alternative splice site (↓) used for generating UNG2 forms (from 45 in human UNG2), the sequences of the two forms are identical in each species. Residues that make up walls of the uracil-binding pocket or which are directly involved in catalysis are marked with a star (★). Residues that are involved in DNA-binding (except those involved in uracil-binding) are marked with a triangle (▼); and FIG. 7 shows the subcellular localization in HeLa cells of UNG2-EGFP-N1 and UNG1-EGFP-N1 fusion products.

HeLa cells were transfected with constructs expressing pUNG2-EGFB-N1 (C), pUNG1-EGFP-N1 (D) or the control pEGFP-N1 (A), all expressed from the CMV promoter, and processed for confocal microscopy. Panel B shows staining of mitochondria with Texas red.

EXAMPLE 1

Site Directed Mutagenesis of Human UDG Codons

Site directed mutagenesis was performed on the relevant codons in human UDG and the proteins expressed in *Escherichia coli*.

Methods

Site-directed mutagenesis was carried out as in Mol et al., 1995, supra. To obtain the Tyr147Ala mutant, codon 147, TAT→Tyr, was changed to GCT→Ala, and to obtain the Asn204Asp mutant, codon 204, AAC→Asn, was changed to GAC→Asp. Mutated DNA fragments were subcloned into human UDG expression construct pTUNGΔ84 by replacing restriction fragments in the expression construct by fragments containing the respective mutations. In *Escherichia coli* pTUNGΔ84 expresses high levels of a fully active human UDG (UNGΔ84) lacking 7 non-essential and non-conserved $NH_2$-terminal residues of the mature form of UDG (Mol et al., 1995, supra; Slupphaug et al., 1995, supra). Expression of mutant proteins in *Escherichia coli* and purification of the mutant proteins to apparent homogeneity were carried out as described previously (Mol et al., 1995, supra; Slupphaug et al., 1995, supra). Relevant fractions were assayed for DNA glycosylase activity during each step in the purification. As a result of high expression, purification may also take advantage of the UV absorption of the enzymes. Peaks of UV absorption corresponding to the enzyme of interest could already be observed after only the first two column steps.

To test enzymatic substrate specificities, 250 ng purified human "wild type" UDG (UNGΔ84), UNGΔ84Tyr147Ala or UNGΔ84Asn204Asp, were mixed with 200 ng ds- or ss-[$^3$H] cytosine-labelled DNA (150 mCi/mmol), or ds- or ss-[$^3$H] thymine-labelled DNA (100 mCi/mmol) in 10 mM NaCl, 20 mM Tris-HCl (pH 7.5), 1 mM EDTA, 1 mM dithiothreitol and 0.5 mg/ml bovine serum albumin (final concentrations) in 20 µl separate reactions. The final concentrations of the [$^3$H] cytosine-DNA (C) and [$^3$H]thymine-DNA (T) substrates were 6.5 µM and 10 µM, respectively. Release of radioactivity as a function of time was measured at 37° C. These conditions are later referred to as standard conditions. Substrate synthesis and processing of samples for scintillation counting were as described in Krokan and Wittwer (1981) Nucl. Acids Res., 9: 2599-2613. Single-stranded substrate was generated by boiling double-stranded substrate for 10 min, followed by rapid cooling on ice.

Results

FIG. 1 demonstrates time-dependent release of acid-soluble radioactivity by homogeneous UNGΔ84Asn204Asp (CDG) from [$^3$H]cytosine-labelled DNA, but not from [$^3$H] thymine-labelled DNA. Conversely, the homogeneous UNGΔ84Tyr147Ala (TDG) mutant releases acid-soluble radiolabelled material from [$^3$H]thymine-labelled DNA, but not from [$^3$H]cytosine-labelled DNA.

EXAMPLE 2

Analysis of the Radioactive Excision Products by Thin Layer Chromatography

Methods

The analysis was performed using DC-cellulose as the stationary phase and methanol:HCl:$H_2O$-70:20:10 as the mobile phase. Samples were prepared as follows: 1.5 µg enzyme (UNGΔ84, UNGΔ84Tyr147Ala or UNGΔ84Asn204Asp as prepared in Example 1) was incubated with 1 µg [$^3$H]uracil-labelled DNA (500 mCi/mmol), [$^3$H]cytosine-labelled DNA (150 mCi/mmol) or [$^3$H]thymine-labelled DNA (100 mCi/mmol) in separate 50 µl reactions under standard buffer conditions (see Example 1) for 1 hour. Macromolecules in the samples were then ethanol precipitated, the supernatants after centrifugation were collected, ethanol was removed by evaporation and the remaining material was dissolved in 10 µl $H_2O$. 1 µl was spotted on the membrane. After migration the cellulose sheet was cut in strips and radioactivity measured by scintillation counting in Ready Protein scintillation cocktail.

Results

Separation of the acid-soluble radioactive material by thin layer chromatography (FIG. 2) demonstrated that the released material was the free bases [$^3$H]cytosine or [$^3$H] thymine. Separation using another mobile phase (butanol:$H_2O$, 86:14) verified these results (data not shown). In addition, both mutants release [$^3$H]uracil, whereas "wild type" UDG (UNGΔ84) releases [$^3$H]uracil only (FIG. 2).

EXAMPLE 3

Substrate Specificity and Uracil Inhibition and Kinetic Properties of UDG-Mutants Methods For measuring release of uracil from double-stranded (U-ds) or single-stranded (U-ss) DNA the various mutant enzymes (prepared as described in Example 1 and by analogous site-directed mutagenesis methods and identical expression and purification methods) were incubated with 200 ng ds- or ss- [$^3$H]dUMP-labelled DNA (500 mCi/mmol, 2 µM final concentration) in 20 µl separate reactions for 10 min under standard conditions as described in Example 1. For measuring release of [$^3$H]cytosine or [$^3$H]thymine, assays were performed as described in Example 1 using an incubation time of 10 min. Uracil inhibition was analysed by adding 5 mM uracil (final concentration) to a standard U-ds assay. 0 activity indicates activity below detection limit (10 pmol per mg protein per min) with 100 ng enzyme and 200 ng DNA substrate at standard conditions.

The kinetic parameters were determined using six different substrate concentrations to obtain the $K_m$ and $V_{max}$ values. Duplicate samples were incubated for 20 min using standard assay buffer conditions and substrates as specified. $K_m$ and $V_{max}$ were calculated using the computer program Enzpack, version 3.0 after the method of Wilkinson (1961) Biochem. J., 80: 324-332. $K_{cat}$ was calculated from $V_{max}$ assuming an $M_r$=25000.

Results

The results are shown in Tables 1 and 2. From Table 1 it can be seen that only the substitution Tyr147Ala results in an enzyme which specifically excises thymine. Similarly, only the substitution Asn204Asp results in a mutant which excises cytosine. Both mutant enzymes exhibit activity on single or double-stranded DNA and are also able to excise uracil. From Table 2 it can be seen that the turnover numbers of CDG and TDG are lower than for "wild type" release of uracil.

Discussion

These results demonstrate the significance of Asn204 for specific binding of uracil-containing DNA and the significance of Tyr147 side chain ring structure for preventing binding of thymine.

It is somewhat surprising that the novel CDG of the invention still recognizes uracil, considering the unfavourable proximity of the Asp carboxyl side chain and the O4 atom in uracil. However, it should be noted that the other oxygen atom of the Asp204 carboxyl side chain still may form H-bonds with N3 uracil and that Asp145 main chain carbonyl as well as the amide-N of Asp145 and Gln144 also contribute to the specificity. In addition, the UDG activity remaining is very low (0.04-0.16%) compared with "wild type". CDG has a 10-fold increased preference for single stranded substrate, whereas TDG has a decreased preference (FIG. 1 and Table 1).

It is evident that the turnover numbers ($K_{cat}$) of the novel enzymes releasing either cytosine or thymine, as well as residual UDG activities, are very low when compared with release of uracil by "wild type" UDG (Table 2). However, the very high turnover number of UDG appears to be unique among DNA glycosylases and turnover numbers of other DNA glycosylases may be as low, or even lower than those of the engineered glycosylases CDG and TDG. Thus, a recent biochemical characterisation of recombinant N-methylpurine-DNA glycosylase from mouse gave $K_{cat}$ values of 0.8 $min^{-1}$ and 0.2 $min^{-1}$ for excision of 3-methyladenine and 7-methylguanine respectively (Roy et al. (1994) Biochemistry, 33: 15131-15140).

The *Escherichia coli* inducible 3-methyladenine-DNA glycosylase II (AlkA) is a DNA glycosylase that recognizes at least 6 different damaged bases, among these structurally different alkylated purines and pyrimidines. The turnover number for AlkA on the substrate 3-methyladenine-DNA is calculated to be 0.03 $min^{-1}$ (Bjelland et al. (1994) J. Biol. Chem., 269: 30489-30495).

The FPG protein (formamido-pyrimidine-DNA glycosylase) also has a rather low turnover number. The $K_{cat}$ value on the imidazole ring-opened form of 7-methylguanine-DNA substrate is calculated to 1.4 $min^{-1}$ (Boiteux et al. (1990) J. Biol. Chem., 265: 3916-3922). A low rate of catalysis is also likely for the naturally occurring T(U)/G-mismatch-DNA glycosylase since band shifts can be demonstrated after mixing the enzyme with substrate (Sassanfar & Roberts (1990) J. Mol. Biol., 212: 79-96).

All of these DNA glycosylases recognize at least two different substrates, and in most cases several damaged pyrimidines or purines. Probably the very high turnover number of UDG reflects a high selectivity of substrate binding in a tight fitting active site, allowing rapid catalysis by this specialized enzyme. In contrast, the DNA glycosylases with a broader substrate specificity may bind substrate less accurately, and excise the base, more slowly.

TABLE 1

| Mutant | pmol excised per min per mg protein | | | | | | Inhibition 5 mM Uracil |
|---|---|---|---|---|---|---|---|
| | U-ds | U-ss | C-ds | C-ss | T-ds | T-ss | % |
| ←Wild type→ | $4.7 \times 10^7$ | $9.5 \times 10^7$ | 0 | 0 | 0 | 0 | 80 |
| Gln144Leu | $3.4 \times 10^4$ | $4.8 \times 10^4$ | 0 | 0 | 0 | 0 | 25 |
| Asp145Glu | $5.5 \times 10^4$ | $8.5 \times 10^4$ | 0 | 0 | 0 | 0 | 80 |
| Asp145Asn | $1.4 \times 10^4$ | $1.1 \times 10^4$ | 0 | 0 | 0 | 0 | 80 |
| Tyr147Ala | $2.2 \times 10^4$ | $2.2 \times 10^4$ | 0 | 0 | $1.3 \times 10^3$ | $7.5 \times 10^2$ | 0 |
| Tyr147Phe | $3.2 \times 10^7$ | $6.3 \times 10^7$ | 0 | 0 | 0 | 0 | 50 |
| Ser169Ala | $3.1 \times 10^6$ | $5.6 \times 10^6$ | 0 | 0 | 0 | 0 | 80 |
| Asn204Asp | $1.7 \times 10^4$ | $1.6 \times 10^5$ | $3.0 \times 10^2$ | $3.0 \times 10^3$ | 0 | 0 | 0 |
| Asn204Gln | $1.5 \times 10^6$ | $2.2 \times 10^6$ | 0 | 0 | 0 | 0 | 70 |
| His268Leu | $1.3 \times 10^5$ | $2.6 \times 10^5$ | 0 | 0 | 0 | 0 | 75 |

TABLE 2

| | Substrate | | | | | | | | | | | |
|---|---|---|---|---|---|---|---|---|---|---|---|---|
| | C-ds | | C-ss | | T-ds | | T-ss | | U-ds | | U-ss | |
| Mutant | $K_m$ (μM) | $K_{cat}$ ($min^{-1}$) | $K_m$ (μM) | $K_{cat}$ ($min^{-1}$) | $K_m$ (μM) | $K_{cat}$ ($min^{-1}$) | $K_m$ (μM) | $K_{cat}$ ($min^{-1}$) | $K_m$ (μM) | $K_{cat}$ ($min^{-1}$) | $K_m$ (μM) | $K_{cat}$ ($min^{-1}$) |
| ←Wild type→ | — | — | — | — | — | — | — | — | 0.10 | 2500 | 0.06 | 5150 |
| Tyr147Ala | — | — | — | — | 6.0 | 0.06 | 1.4 | 0.02 | 3.5 | 1.0 | 0.30 | 0.6 |
| Tyr147Phe | — | — | — | — | — | — | — | — | 0.16 | 1225 | 0.10 | 2370 |
| Asn204Asp | 35 | 0.12 | 5.3 | 0.39 | — | — | — | — | 2.4 | 1.2 | 2.0 | 15 |
| Asn204Gln | — | — | — | — | — | — | — | — | 0.40 | 66 | 0.23 | 89 |

EXAMPLE 4

Effects of TDG and CDG Activity on Frequency of Rifampicin Resistant Mutations in *E. coli* ung+ Strain (NR8051) and *E. coli* ung− Strain (NR8052)

Methods

An overnight culture of *E. coli* strains NR8051 and NR8052 (both reCA+, provided by Tomas Kunkel of National Institute of Environmental Health, USA) containing plasmids pTrc99A, pTUNGΔ84, UNGΔ84Tyr147Ala and UNGΔ84Asn204Asp were prepared as described in Example 1 and grown in LB-medium with ampicillin (100 µg/ml) at 30° C. The culture was then diluted 1:20 in fresh medium and cultured for 5 hours at 37° C. Induced culture contained 1 mM IPTG in the LB-medium. To determine the number of rifampicin resistant bacteria, 100 µl of the culture were mixed with 3 ml top agarose and poured on LB plates containing 100 µg/ml rifampicin and incubated overnight at 37° C. Colonies were counted and the number of rifampicin resistant colonies per $10^8$ viable cells was calculated.

Results

The results are shown in Table 3. These results indicate that the expression of UDG does not cause an increase in mutation frequencies (plasmid pTUNGΔ84 compared to parental pTrc99A). In fact, human UDG complements *E. coli* ung− cells. This is clear from the reduction in mutation frequencies from 4.4 to 1.3 when UDG is present in induced cells. Uninduced cells are also protected as a result of promoter leakage. In contrast, the mutation frequencies of *E. coli* ung+ cells are increased by a factor of 8.6 and 39 when carrying plasmids encoding CDG and TDG, respectively, compared to host cells carrying the parental plasmid pTrc99A. This increases to approximately 8.9 and 94.4 respectively, in induced ung+ cells.

Discussion

Single amino acid substitutions transform the highly uracil-selective uracil-DNA glycosylase into less selective DNA glycosylases that attack normal pyrimidines and confer a mutator phenotype upon the cell, presumably because excess numbers of apyrimidinic-sites are formed.

It may seem surprising that propagation of plasmids expressing CDG or TDG activity is at all possible, since they might be expected to kill the host cells. We believe that the relatively low turnover numbers and the low expression in the absence of inducer (IPTG) is sufficient to reduce the number of depyrimidinations to a level that the DNA repair system can cope with. Nevertheless, DNA degradation is detectable even in the absence of inducer and is strongly increased when IPTG is added (data not shown). The survival of *Escherichia coli* recA+ host cells carrying uninduced CDG or TDG-plasmid is equal to that of the parental cell carrying plasmid pTrc99A (data not shown) although mutation frequencies are increased by a factor of 8.6 and 39 for CDG and TDG, respectively as mentioned above.

Induction of CDG or TDG by IPTG reduces survival of the *Escherichia coli* host cells (in both NR8051 and NR8052) to less than 50% and 10%, respectively, within 5 hrs. Thus, AP-site repair capacity is sufficient for repair of damage caused by expression of CDG or TDG due to "leakage" from the uninduced promoter. However, this repair is apparently not complete, or may be inaccurate, since the frequency of mutations leading to rifampicin resistance is significantly increased by induction with IPTG (Table 3). The activity of TDG in vivo leads to a 10-fold higher mutation frequency in *Escherichia coli* than the in vivo CDG activity. This probably reflects the fact that TDG has a higher activity on dsDNA than CDG, as demonstrated by in vitro experiments with homogeneous enzyme (FIG. 1), and that the $K_m$ value for TDG on dsDNA is much lower than the $K_m$ for CDG on dsDNA (Table 2). We have observed that TDG and CDG are both highly cytotoxic in a recA− background (*Escherichia coli* DH5α) even without induction (data not shown). It is likely that this cytotoxic effect is due to a lack of SOS-induction in recA− cells. The chemical nature of the SOS-inducing signal, or signals, is not fully known, and some DNA lesions may indirectly activate the SOS response by interfering with DNA replication (Sassanfar & Roberts, 1990, supra). If generation of AP-sites by TDG and CDG directly or indirectly triggers SOS-induction, this would increase cell survival, at the cost of error prone repair and a high yield of mutations. CDG and TDG should be very useful for exploring the biological consequences of AP-sites in DNA.

The new DNA glycosylases that we have engineered are distinctly different from previously known glycosylases. The mismatch-specific thymine-DNA glycosylase previously reported also releases uracil (Sassanfar & Roberts, 1990, supra; Nedderman & Jiricny, 1993, supra), like the thymine-DNA glycosylase we have constructed. However while the naturally occurring thymine-DNA glycosylase has an absolute requirement for a mismatched U or T opposite of a G, the TDG we have engineered recognises T or U from T(U):A matches, as well as from single stranded substrate. A DNA glycosylase recognizing unmodified cytosine had previously not been reported.

The mutator phenotype caused by a single amino acid substitution is intriguing since it changes an enzyme from its normal role in mutation avoidance into a cytotoxic mutator protein. In the case of CDG this change is the result of a single A→G transition, which in vivo could be the result of several different events, such as deamination of A, O4-alkylation of T in the complementary strand, and replication errors. Since this mutation would be dominant, only one allele would need to be mutated to get a new phenotype. It is possible, however, that this mutation would be lethal, or that it would be without serious consequences due to efficient repair of DNA in mammalian cells. Nevertheless, the generation of repair enzymes having a dominant mutator effect that would give the cells a hypermutable phenotype may represent a new principle in mutagenesis.

TABLE 3

| | Frequency of rif$^R$ mutations per $10^8$ cells | | | |
|---|---|---|---|---|
| | NR8051 | | NR8052 | |
| Plasmid | Uninduced | Induced | Uninduced | Induced |
| pTRC99A | 0.8 ± 0.3 | 0.9 ± 0.5 | 4.2 ± 1.2 | 4.4 ± 1.1 |
| pTUNGΔ84 | 0.7 ± 0.4 | 0.8 ± 0.3 | 0.9 ± 0.2 | 1.3 ± 0.4 |
| pTUNGΔ84Tyr147Ala | 31 ± 8 | 85 ± 32 | 13 ± 5 | 57 ± 9 |
| pTUNGΔ84Asn204Asp | 6.9 ± 4.1 | 8.0 ± 3.4 | 2.1 ± 0.7 | 4.1 ± 1.1 |

EXAMPLE 5

Effects of TDG Activity on the Frequency of Rifampicin Resistant Mutations in *E. coli* Strains BW527, and GW2100 (umuC−)

An overnight culture of *E. coli* strains BW527 (endoIV−) or GW2100 (umuC−) provided by Erling Seeberg, The National Hospital, Oslo, containing plasmids pTrc99A or UNGΔ84Tyr147Ala (TDG) were prepared as described in Example 1 and grown in LB-medium with ampicillin (100 µg/ml) at 30° C. The culture was then diluted 1:20 in fresh medium and cultured as described in Example 4.

Results

The results are shown in Table 4. These results indicate that the expression of UNGΔ84Tyr147Ala (TDG) in *E. coli* strains BW527 (endoIV$^-$) or GW2100 (umuC$^-$) enhances the mutagenic effect of TDG compared to strains that do not carry these defects in the repair of AP-sites or defect in umuC especially after induction with IPTG. pTrc99A alone did not exert this effect to any significant extent. Even more importantly, the background mutations in these strains are low and the effects of induction with IPTG is high, thus improving the usefulness of UNGΔ84Tyr147Ala (TDG) for mutagenesis when using more optimal strains.

These results are especially surprising in light of previous findings that mutants in umuC are generally difficult to mutate by some methods, for example by UV-light or by chemical challenge.

carried out at 65° C. overnight in 6×SSC, 5×Denhardt's solution and 0.1% SDS. Filters were washed in 0.1×SSC/0.5% SDS at 65° C. and autoradiographed. Three rounds of screening were done. In vivo excision of pBluescript phagemids from the Uni-ZAP™XR vector was performed as recommended by the manufacturer.

Sequence Analysis of Clones

Sequencing was performed on an Applied Biosystems Model 373A DNA Sequencing System using the Dye terminator cycle sequencing ready reaction kit as recommended by the manufacturer. The sequences were analysed using the Auto Assembler software (Applied Biosystems).

In Vitro Transcription, Uracil-DNA Glycosylase Assays and Transient Transfection of HeLa Cells for Promoter Studies In vitro transcription/translation was performed with the TNT transcription/translation system with [$^{35}$S]methionine as recommended by the manufacturer, using 200 ng of the expression constructs per 10 µl reaction volume. The mouse UNG1-pBluescript construct was transcribed from the T3

TABLE 4

Effects of TDG-activity on frequency of rifampicin resistant mutations in *E. coli* strains BW527 and GW2100

| | Frequency of rif$^R$ mutations per $10^8$ cells | | | |
|---|---|---|---|---|
| | BW527 | | GW2100 | |
| Plasmid | Uninduced | Induced | Uninduced | Induced |
| pTRC99A | 0.06 ± 0.02 | 0.07 ± 0.03 | 0.24 × 10$^{-3}$ ± 0.1 × 10$^{-3}$ | 6 × 10$^{-3}$ ± 5 × 10$^{-3}$ |
| pTUNGΔ84Tyr147Ala | 1.20 ± 0.2 | 240 ± 122 | 0.65 ± 3829 | 84 ± 28 |

EXAMPLE 6

Isolation and Characterisation of a Nuclear Form of Uracil-DNA Glycosylase

Materials and Methods

Materials

Mouse embryonic carcinoma cDNA library, human liver cDNA library and NT2 neuronal precursor cell cDNA library were from Stratagene (La Jolla, Calif., USA). All libraries were propagated in the Uni-ZAP™XR vector using XL-1 blue as host. [α-$^{32}$P]dCTP, [$^{35}$S]methionine, Rediprime random labelling kit and Hybond N+ filters were all from Amersham (UK). All sequencing primers were from MedProbe (Oslo, Norway). Dye terminator cycle sequencing ready reaction kit was from Applied Biosystems (Foster City, Calif.). The Dynazyme PCR kit was purchased from Finnzymes Oy (Espoo, Finland). TNT in vitro transcription/translation rabbit reticulocyte lysate system kit, pGEM-T TA cloning kit, Alter Sites II in vitro Mutagenesis System, primers for sequencing from T3 and T7 promoters and T3 RNA polymerase were from Promega (Madison, Wis.). The plasmid encoding the red-shifted variant of green fluorescent protein (pEGFP-N1) was from Clontech (Palo Alto, Calif., USA). Restriction enzymes were from New England Biolabs Inc. (Beverly, Mass., USA).

Screening of cDNA Libraries

All libraries were screened as recommended by the manufacturer, using $^{32}$P-labelled UNG40 cDNA (Olsen et al., 1989, EMBO J., 8, p 3121-3125) as probe. Hybridization was promoter in the pBluescript vector. The insert of mouse UNG2-pBluescript was amplified by the polymerase chain reaction using Dynazyme PCR kit, ligated into the pGEM-T vector and transcribed from the T7 promoter. The human UNG2-pBluescript was transcribed from the T3 promoter after SacI/NheI excision of a 79 bp fragment from the polylinker and the 5'-end of cDNA for UNG2. Human UNG1 cDNA was transcribed from the T7 promoter as previously described (Slupphaug et al., 1995, Biochemistry, 34, p 128-138). The samples were run on a 12% denaturing sodium dodecyl sulfate polyacrylamide gel (SDS-PAGE). The gel was dried, autoradiographed overnight and scanned on an LKB Ultroscan XL Enhanced Laser Densitometer. Uracil-DNA glycosylase activity was measured in parallel samples of the in vitro transcription/translation assay mixture containing unlabelled amino acids (Slupphaug et al., 1995, supra). A construct containing both promoters (pGL2-ProAB) linked to the luciferase gene was prepared by insertion of a PvuII/MluI fragment (the enzymes cleave in positions 418 and 1035, respectively) from the promoter region of the UNG gene into the SmaI-MluI sites of pGL2-ProB. A promoter II-luciferase construct (pGL2-ProB) and transient transfection with Transfectam (Promega) have been described previously (Haug et al., 1994, FEBS Letters, 353, p 180-184).

Preparation of pUNG-EGFP-N1 Fusion Constructs and Localization Studies

UNG15 cDNA, which encodes UNG1, in pGEM7Zf+ (pUNG15), (Slupphaug et al., 1995, supra; Olsen et al., 1989, supra) was digested with BclI, which cuts at bp 1019 in UNG15 cDNA, blunted with DNA polymerase I, (Klenow fragment), and ligated to an AgeI linker prepared from the oligonucleotide 5'-ACCGGTGCC-3' and its complementary copy. The religated pUNG15 containing the AgeI linker correctly ligated into the BclI site (verified by sequencing) was digested with RsrII, which cuts at bp 49 in UNG15 cDNA (Olsen et al., 1989, supra), blunted as above and finally digested with AgeI. The fragment was then ligated into pEGFP-N1 digested with SmaI (blunt) and AgeI. The construct was sequenced to verify that the construct was in frame with the ATG of the EGFP-N1 fusion protein. The TGA stop codon of pUNG15 was changed to GGA by site-directed mutagenesis performed according to the procedure provided by the manufacturer using ssDNA prepared with R408 phage. Potential pUNG1$_{GGA}$-EGFP-N1 constructs were screened by digestion with BclI (digests only unmutated plasmids) and verified by sequencing. The correct construct was named pUNG1-EGFP-N1. cDNA for UNG2 (this example) in pBluescript was digested with NheI, which cuts 54 bp upstream of ATG, and EcoNI which cleaves the cDNAs in the sequence that is shared by cDNAs for UNG1 and UNG2 (positions 529 and 520, respectively). The resulting fragment of interest (501 bp) was isolated and ligated to the 5155 bp fragment of KheI/EcoNI-digested pUNG1-EGFP-N1 to obtain pUNG2-EGFP-N1. Transient transfections of HeLa cells were done with the CaPO$_4$-method (Profection, Promega) according to the manufacturer's recommendations. Confocal microscopy (BioRad MRC-600) of HeLa cells and staining of mitochondria with mouse anti human mitochondria antibody (MAB 1273, Chemicon) and Texas Red anti-mouse IgG (Vector) were performed as previously described (Nagelhus et al., 1995, Exptl. Cell Res., 220, p 292-297). Examination of HeLa cells transfected with expression plasmids pEGFP-N1, pUNG1-EGFP-N1 or pUNG2-EGFP-N1 was carried out using an excitation wave length of 488 nm and emission wave length >515 nm at 16 hours after transfection Results A human NT2 neuronal precursor cell cDNA library and a mouse embryonic carcinoma cDNA library were screened and a new form of human uracil-DNA glycosylase (human UNG2) encoded by the UNG gene, as well as the homologous cDNA from mouse (mouse UNG2) was identified. In addition the cDNA for the mouse homolog (encoding mouse UNG1) of human UNG1 (Olsen et al., 1989, supra) was identified. cDNA for human UNG2 has an ORF encoding 44 N-terminal amino acids not found in human UNG1 whereas cDNA for human UNG1 has an ORF encoding 35 amino acids not found in human UNG2 (FIG. 4). The two forms are identical in the rest of the amino acid presequence, which is not required for enzyme activity, as well as in the catalytic domain, altogether 269 identical consecutive amino acids. The sequence of the 269 amino acids common to UNG1 and UNG2, and the corresponding DNA sequence, is identical to amino acid residues 35-304 in Olsen et al., 1989, supra. cDNAs for human UNG2 and its mouse homolog, are apparently as abundant as UNG1 in cDNA libraries from proliferating cells since among 20 cDNA clones that were sequenced 10 were of the UNG2 type and 10 were similar to the previously known UNG1 type. Among 4 mouse cDNAs sequences, 3 were of the UNG2 type and 1 was of the UNG1 type. However, screening of a human hepatocyte library with UNG40 cDNA resulted in the isolation of 80 strongly hybridizing clones and sequencing of 14 of these demonstrated that they were all similar to the previously characterized cDNA for UNG1 or the cDNA UNG40 (Olsen et al., 1989, supra).

Comparison of the human cDNA for UNG2 with the recently published complete human UNG sequence (Haug et al., 1996, Genomics, 36, p 408-416) revealed the presence of a previously unrecognised exon (exon 1A) located some 650 base pairs upstream of the previously identified exon 1 (hereinafter called exon 1B). A revised organization of the UNG gene is therefore presented in FIG. 3. Exon 1B forms the leader sequence and codon 1-104 of the mRNA encoding the previously known form UNG1. The mRNA corresponding to the new human cDNA is formed by joining exon 1A (encoding 44 amino acids) into a consensus splice site after codon 35 in exon 1B after which the two human cDNAs are identical. The open reading frame of human UNG2 cDNA predicts a protein of 313 amino acids, as compared to 304 amino acids for UNG1. Genomic clones for the mouse homolog of the UNG gene have also been isolated and sequenced. This has revealed that the splice sites for exons 3, 4, 5 and 6 in the UNG genes from mouse and man are in identical positions. Furthermore, PCR analyses have demonstrated that the rest of the mouse gene is structurally similar to the human gene, as expected from the cDNA clones (data not shown).

FIG. 4 shows how the alternative forms of mRNA for UNG1 and UNG2 arise as deduced from human cDNAs and the corresponding UNG sequences and indicates the presence of a putative nuclear localization signal of 4 basic residues (RKRH) in the N-terminal end of the new cDNA and putative mitochondrial localization signals in cDNA for UNG1. In addition, and now shown here, both human cDNAs contain a putative nuclear localization signal (RKRHH) in the catalytic domain (residues 258-262 in the ORF of cDNA for UNG1). These residues are located at the surface of the enzyme between α-helix 7 and β-strand 4 (Mol et al., 1995, Cell, 80, p 869-878)

FIG. 5 shows the genomic structure of exons 1A and 1B, as well as the structure of the previously characterized promoter (hereinafter called promoter II), possible elements in the putative promoter upstream of exon 1A (hereinafter called promoter I) and the alternative splice acceptor site (SEQUENCE I.D. No. 7). Promoter I probably starts after the 3'-terminal end of two Alu-repeats (position 425) and ends immediately upstream of the start of exon 1A. However, it can not be excluded that the promoter is located upstream of the Alu-repeats. This would require the presence of an exon encoding a leader that would be joined to exon 1A. This is considered unlikely since promoter motifs upstream of the Alu-repeats have not been detected and furthermore transcripts of the required size have also not been detected by Northern analyses (data not shown). Furthermore, the cDNA for UNG2 does not contain sequences from this upstream region.

FIG. 6 shows an alignment of predicted amino acid presequences of the human and mouse enzymes (SEQUENCE I.D. Nos 2 and 8-10). Note that UNG1 proteins and UNG2 proteins have been aligned separately in the parts of the proteins that are derived from different exons (up to codon 45 in human UNG2). Table 4 shows the % of identical residues in the different forms, using human UNG2 as the reference (100%). The parts of the protein that are not required for catalytic activity are less well conserved than the catalytic domain. Amino acids that have been found to be critical for catalytic activity or formation of the uracil-binding pocket (Mol et al., 1995, supra; Kavli et al., 1996, EMBO J., 15, p 3442-3447) or DNA binding are completely conserved in mouse (residues Q144, D145, P146, Y147, F158, S169, N204, S247, H268, S270, L272, S273, Y275 and R276 in UNG1).

To compare the promoter activity of promoter I alone and promoter I and promoter II in combination, promoter-luciferase gene constructs were prepared and transient transfection experiments performed with HeLa cells. These studies verified the promoter activity of promoter II alone (Haug et al., 1994, supra) and further demonstrated that when both promoters are present in the construct, the luciferase activity increased some 50%, indicating that promoter I is also active in HeLa cells, as expected from the abundance of the new cDNA in proliferating cells (Table 5).

Coupled transcription-translation of the two forms of human and mouse cDNA resulted in easily measurable uracil-DNA glycosylase activity for both forms from mouse and man. For calculations of the relative specific activities, the radioactivity released in uracil-DNA glycosylase assays was compared to band intensities on an SDS-PAGE gel from transcription/translation reactions using [$^{35}$S] methionine (Table 6).

To examine whether human UNG1 and UNG2 were translocated to different subcellular compartments, constructs expressing fusion proteins of the UNG proteins and a red shifted variant of green fluorescent protein (EGFP-N1) were prepared. These were used for transient transfection experiments with HeLa cells. The major advantage of the green fluorescent protein (over the use of antibodies) is that this method relies on the autofluorescence of this protein alone, and thus possible cross reaction of the antibody with epitopes in irrelevant proteins is not a problem. The control (pEGFP-N1) shows that the green fluorescent protein displays a homogeneous staining over the cells (FIG. 7A). In contrast, the UNG2-EGFP-N1 fusion protein is exclusively located in the nuclei (FIG. 7C) and the UNG1-EGFP-N1 fusion protein (FIG. 7D) is mainly, if not exclusively, located in extranuclear spots that have the same appearance as mitochondria stained with Texas red (FIG. 7B). These results provide convincing experimental evidence that UNG2 is a nuclear protein and UNG1 a mitochondrial protein.

TABLE 4

Conservation of amino acids in four homologs of uracil-DNA glycosylase calculated as % identity with human UNG2*

| | % identity of domains | | | |
|---|---|---|---|---|
| | Variant presequence# (1-44) | Common presequence (45-63) | Catalytic domain (64-313) | Overall identity (1-313) |
| hUNG1 | 2 | 100 | 100 | 90 |
| mUNG2 | 64 | 75 | 91 | 86 |
| mUNG1 | 2 | 75 | 91 | 79 |

*The identity is calculated for the domains in UNG2 compared with the corresponding domains in the other forms.
The identity of the presequences of hUNG1 and mUNG1 is 27% with 82% identity overall.

TABLE 5

Promoter activites in the UNG gene*

| Promoter - reporter gene construct | Luciferase activity % |
|---|---|
| pGL2-Basic | 0.8 ± 0.4 |
| pGL2-ProB | 100 ± 8 |
| pGL2-ProAB | 156 ± 4 |

*The promoter activity of pGL2-ProB (promoter II) was arbitrarily set to 100%. pGL2-Basic is a control lacking promoter.

TABLE 6

Relative specific activities of different forms of UNG after translation in rabbit reticulocyte lysates*

| Protein | dpm* | Area(mm$^2$) | Activity (dpm/area) |
|---|---|---|---|
| human UNG1 | 1291 | 0.054 | 23907 |
| human UNG2 | 6360 | 0.268 | 23731 |
| human UNG1 | 921 | 0.061 | 15098 |
| mouse UNG2 | 856 | 0.051 | 16784 |

*Relative specific activites were calculated from measured dpm-values ($^3$H-uracil released in uracil-DNA glycosylase assays) and areas under the curve of scanned bands on SDS-PAGE gels after subtraction of background values of 123 dpm.

The invention claimed is:

1. An isolated thymine-DNA glycosylase (TDG) which releases thymine bases from single stranded (ss) DNA and double stranded (ds) DNA, said TDG obtainable by modification of a uracil-DNA glycosylase (UDG), wherein said modification consists of replacing tyrosine (Tyr) at amino acid position 147 with a different amino acid in the human UDG protein which protein comprises SEQ ID NO: 8.

2. The TDG as claimed in claim 1 wherein said Tyr is replaced with an alanine residue (Ala).

3. The thymine-DNA glycosylase (TDG) as claimed in claim 1 wherein said TDG releases both thymine and uracil bases from ssDNA and dsDNA.

4. The TDG as claimed in claim 1 wherein said TDG releases thymine bases from A:T DNA pairs.

5. The DNA glycosylase as claimed in claim 1 which additionally comprises at least one nuclear localization peptide sequence encoded by a nucleic acid molecule comprising the sequence (SEQ. ID. No.: 3)
ATGATCGGCC AGAAGACGCT CTACTCCTTT TTCTCCCCCA

GCCCCGCCAG GAAGCGACAC GCCCCCAGCC CCGAGCCGGC

CGTCCAGGGG ACCGGCGTGG CTGGGGTGCC TGAGGAAAGC

GGAGATGCGG CG or a fragment thereof encoding a functional equivalent or a sequence which is degenerate, or which hybridizes under conditions of wash at 2×SSC, 65° C. with any such aforesaid sequence or at least one mitochondrial localization peptide sequence encoded by a nucleic acid molecule comprising the sequence (SEQ. ID. No.: 5)
ATGGGCGTCT TCTGCCTTGG GCCGTGGGGG TTGGGCCGGA

AGCTGCGGAC GCCTGGGAAG GGGCCGCTGC AGCTCTTGAG

CCGCCTCTGC GGGGACCACT TGCAG or a fragment thereof encoding a functional equivalent or a sequence which is degenerate, or which hybridizes under conditions of wash at 2×SSC, 65° C. with any such aforesaid sequence.

6. The DNA glycosylase as claimed in claim 5 wherein said nuclear localizing peptide includes the amino acid sequence wherein RKR is followed by histidine.

7. A method of performing enzymatic DNA sequencing to determine the position of thymine bases comprising the step of treating said DNA with at least one TDG as defined in claim 1.

8. A method of performing in vitro mutagenesis which method comprises introducing one or more TDG of claim 1 to a complex sample comprising a nucleic acid substrate, wherein thymine is removed and optionally replaced in said nucleic acid substrate.

9. A method of performing in vivo mutagenesis which method comprises introducing a TDG of claim 1 into a liposome, and introducing said liposome into a suitable host cell.

10. A method of removing contaminating DNA from a sample prior to PCR amplification, comprising introducing one or more TDG of claim 1 to a reaction mixture, wherein contaminating DNA are digested by said one or more TDG, and
   inactivating said one or more TDG prior to addition of a DNA sample and amplification.

11. A method of producing randomly fragmented DNA comprising introducing one or more TDG of claim 1 to a DNA sample to yield one or more apyrimidinic site(s) (AP-site(s)) in said sample, and
   treating said sample with an alkaline solution alone, an apurinic/apyrimidinic-site endonuclease (AP-endonuclease), or a combination thereof, wherein breaks are produced in the DNA at the AP-site(s) which yield randomly fragmented DNA of defined size ranges.

12. A method to modify DNA which method comprises contacting said DNA with the TDG of claim 1.

* * * * *